US006171591B1

(12) United States Patent
Hall

(10) Patent No.: US 6,171,591 B1
(45) Date of Patent: Jan. 9, 2001

(54) RECOMBINANT NODAVIRUS COMPOSITIONS AND METHODS

(75) Inventor: Stephen G. Hall, San Diego, CA (US)

(73) Assignees: Pentamer Pharmaceuticals, Inc., Anaheim; The Scripps Research Institute, La Jolla, both of CA (US)

( * ) Notice: Under 35 U.S.C. 154(b), the term of this patent shall be extended for 0 days.

(21) Appl. No.: 08/986,659

(22) Filed: Dec. 8, 1997

(51) Int. Cl.⁷ .................................................... A61K 39/12
(52) U.S. Cl. .................... 424/186.1; 424/192.1; 424/199.1; 424/224.1; 435/5; 530/350
(58) Field of Search .................... 530/350; 424/186.1, 424/192.1, 199.1, 224.1; 435/5

(56) References Cited

U.S. PATENT DOCUMENTS

| 4,873,192 | * 10/1989 | Kunkel | 435/172.3 |
| 5,149,650 | 9/1992 | Wertz et al. . | |
| 5,932,426 | * 8/1999 | Baralle et al. | 435/7.2 |

FOREIGN PATENT DOCUMENTS

WO 96/05293   2/1996   (WO) .

OTHER PUBLICATIONS

Kreis, Microinjected antibodies against the cytoplasmic domain of the vesicular stomatitis virus glycoprotein block its transport to the cell surface. The EMBO Journal 5(5):931–941, 1986.*

* cited by examiner

Primary Examiner—Donna C. Wortman
(74) Attorney, Agent, or Firm—Olson & Hierl, Ltd.

(57) ABSTRACT

Recombinant nodavirus related compositions are disclosed. These compositions include chimeric proteins in which a nodavirus capsid protein is present together with a heterologous peptide segment. The heterologous peptide includes at least one cell-specific targeting sequence, such as a B cell epitope, a T cell epitope, or a sequence specific for another cell type, such as a hepatocyte. The chimeric proteins can be assembled to form chimeric virus-like particles. The chimeric virus-like particles are useful in therapeutic applications, such as vaccines and gene-delivery vectors, and in diagnostic applications, such as kits for the testing of body tissue or fluid samples. Methods for the use of recombinant nodavirus related compositions in therapeutic and diagnostic applications are also described.

24 Claims, 15 Drawing Sheets

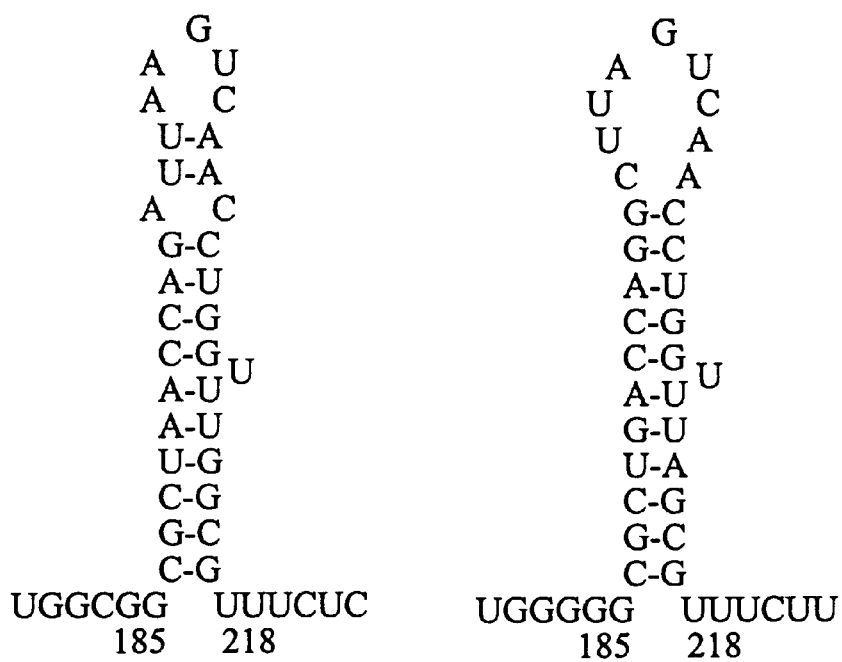
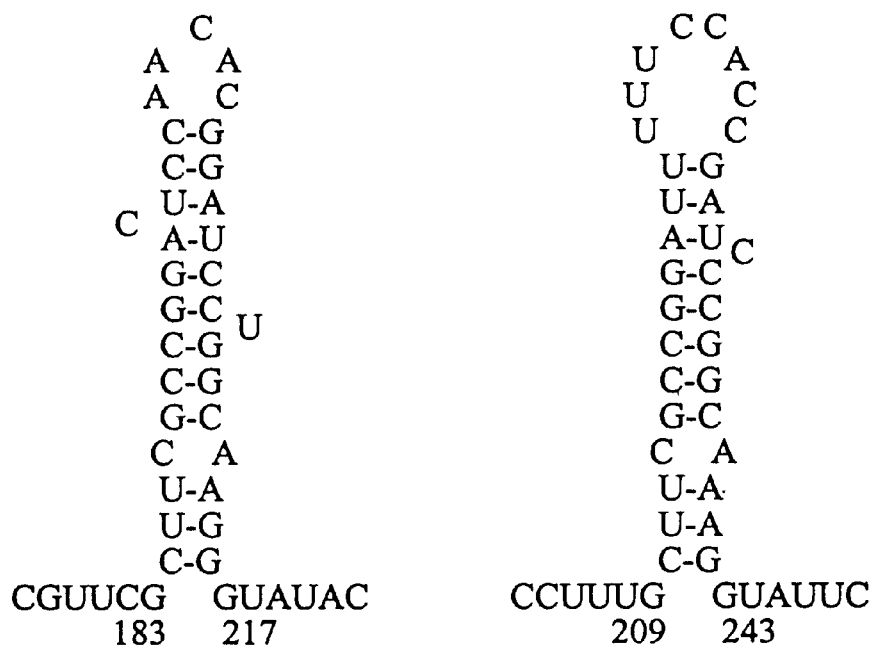
FIG. 2 p2BS(+)-wt Sequence

Sequence immediately flanking the RNA2 insert sequence was determined by sequencing the ends of p2BS(+)-wt, p2BS(+)-RNA2:VSV-G #1, p2BS(+)-RNA2:BRSV #1.

p2BS(+)-wt 5' end (-27 M13 Reverse Primer)

```
         pBS                                RNA2          Start
5'  CC   AAGCT  CGAAATTAACCCTCACTAAA  GTAAACAATTCCAAGTTCCAAAATGGTTAA  3'
3'  GG   TTCGA  CGTTTAATTGGGAGTGATTT  CATTTGTTAAGGTTCAAGGTTTTACCAATT  5'   (SEQ ID NO: 14)
``` p2BS(+)-wt 3' end (-40 M13 Forward Primer)

```
               RNA2               XbaI         ??                          pBS
5'  AAACCAGTTTAAGTCAACAGACTAAGG  TCTAGA  GGATCCCCGGGTACCGAGCTCG  AATTCGCCCTATAGTGAGTCGTATTACAATTCACTGGC  3'
3'  TTTGGTCAAATTCAGTTGTCTGATTCC  AGATCT  CCTAGGGGCCCATGGCTCGAGC  TTAAGCGGGATATCACTCAGCATAATGTTAAGTGACCG  5'
                                         BamHI SmaI KpnI (SEQ ID NO: 15)
```

FIG. 4 p2BS(+)-RNA2:VSV-G Constructs

Used oligonucleotide-mediated mutagenesis to insert the VSV-G coding sequence between RNA2 amino acid residues 207 & 208.

RNA2 Peptide And Coding Sequence:

```
     GGC  CAA  CGT  TGT  CTA.......Peptide........GGT  CGG  TGG  TCA  AGC    (TEMPLATE)
     CCG  GTT  GCA  ACA  GAT....Insertion Site....CCA  GCC  ACC  AGT  TCG     (CODING)
203   P    V    A    T    D                        P    A    T    S    S   (AA SEQUENCE)      (SEQ ID NO: 16)
```

VSV-G Peptide And Coding Sequence:

```
TAC  ACA  GAC  ATC  GAG  ATG  AAC  CGA  CTG  GGA  AAG       (SEQ ID NO: 17)
 Y    T    D    I    E    M    N    R    L    G    K
```

Made several conservative base substitutions to increase GC content.

```
TAC  ACG  GAC  ATC  GAG  ATG  AAC  CGC  CTG  GGC  AAG       (SEQ ID NO: 18)
 Y    T    D    I    E    M    N    R    L    G    K
```

RNA2:VSV-G Peptide And Coding Sequence:

```
3'  GGC CAA CGT TGT CTA..ATG TGC CTG TAG CTC TAC TTG GCG GAC CCG TTC..GGT CGG TGG TCA AGC   (TEMPLATE)
5'  CCG GTT GCA ACA GAT..TAC ACG GAC ATC GAG ATG AAC CGC CTG GGC AAG..CCA GCC ACC AGT TCG    (CODING)
     P   V   A   T   D    Y   T   D   I   E   M   N   R   L   G   K    P   A   T   S   S  (AA SEQUENCE)

(SEQ ID NO: 19)
```

FIG. 5

RNA2:VSV-G Mutagenic Primer and Hybridization Probe Because of the way that the RNA2 cDNA is cloned into the M13(m p2BS(+)-RNA2:BRSV Constructs Used oligonucleotide-mediated mutagenesis to insert a 26 amino acid BRSV coding sequence between RNA2 amino acid residues 207 & 208.

RNA2 Peptide And Coding Sequence:

```
     GGC  CAA  CGT  TGT  CTA.......Peptide.........GGT  CGG  TGG  TCA  AGC    (TEMPLATE)
     CCG  GTT  GCA  ACA  GAT....Insertion Site.....CCA  GCC  ACC  AGT  TCG     (CODING)
203   P    V    A    T    D                         P    A    T    S    S   (AA SEQUENCE)    (SEQ ID NO: 16)
```

BRSV Peptide And Coding Sequence:

```
     GAC  AAA  GAG  CTT  CTA  CCT  AAA  GTT  AAC  AAT  CAT  GAT  TGT ...
200  Asp  Lys  Glu  Leu  Leu  Pro  Lys  Val  Asn  Asn  His  Asp  Cys

CAG  ATA  TCC  AAC  ATA  GCA  ACT  GTG  ATA  GAA  TTC  CAA  CAA
213  Gln  Ile  Ser  Asn  Ile  Ala  Thr  Val  Ile  Glu  Phe  Gln  Gln         (SEQ ID NO: 22)
```

RNA2:BRSV Peptide And Coding Sequence:

```
3'  GGC  CAA  CGT  TGT  CTA ...
5'  CCG  GTT  GCA  ACA  GAT ...
     P    V    A    T    D

CTG  TTT  CTC  GAA  GAT  GGA  TTT  CAA  TTG  TTA  GTA  CTA  ACA ...
    GAC  AAA  GAG  CTT  CTA  CCT  AAA  GTT  AAC  AAT  CAT  GAT  TGT ...
    Asp  Lys  Glu  Leu  Leu  Pro  Lys  Val  Asn  Asn  His  Asp  Cys

GTC  TAT  AGG  TTG  TAT  CGT  TGA  CAC  TAT  CTT  AAG  GTT  GTT ...
    CAG  ATA  TCC  AAC  ATA  GCA  ACT  GTG  ATA  GAA  TTC  CAA  CAA ...
    Gln  Ile  Ser  Asn  Ile  Ala  Thr  Val  Ile  Glu  Phe  Gln  Gln    GGT  CGG  TGG  TCA  AGC    (TEMPLATE)
                                                                       CCA  GCC  ACC  AGT  TCG     (CODING)
                                                                        P    A    T    S    S   (AA SEQUENCE)

(SEQ ID NO: 23)
```

FIG. 7

RNA2:BRSV Mutagenic Primer

Because of the way that the RNA2 cDNA is cloned into the M13(mp18) vector DNA, the M13:RNA2 phage ssDNA contains the RNA2 coding sequence. The mutagenic primer therefore has to be the template sequence (5' to 3'), which is the template sequence in the above figure, read backwards. A hybridization probe was used to detect mutagenized clones by plaque hybridization.

The mutagenic primer (BRSV-P) is therefore:

5' CGA ACT GGT GGC TGG ...

TTG TTG GAA TTC TAT CAC AGT TGC TAT GTT GGA TAT CTG ...

ACA ATC ATG ATT GTT AAC TTT AGG TAG AAG CTC TTT GTC ...

ATC TGT TGC AAC CGG 3' (108 mer) (SEQ ID NO: 24)

RNA2:BRSV hybridization probe (BRSV-H):

5' CAC AGT TGC TAT GTT GGA TAT CTG ACA ATC ATG 3' (33 mer) (SEQ ID NO: 25)

Primers as synthesized

(BRSV-P, 108 mer)

```
5'   CGA  ACT  GGT  GGC  TGG  TTG  TTG ..
     GAA  TTC  TAT  CAC  AGT  TGC  TAT ..
     GTT  GGA  TAT  CTG  ACA  ATC  ATG ..
     ATT  GTT  AAC  TTT  AGG  TAG  AAG ..
     CTC  TTT  GTC  ATC  TGT  TGC  AAC ..
     CGG                                3'
```

(SEQ ID NO: 24)

(BRSV-H, 33 mer)

```
5'   CAC  AGT  TGC  TAT  GTT  GGA  TAT ..
     CTG  ACA  ATC  ATG                 3'
```

(SEQ ID NO: 25)

FIG. 8

Construction of pVL1392-RNA2, pVL1392-RNA2:VSV-G & pVL1392-RNA2:BRSV Baculovirus Expression Vectors.

Designed PCR primers based on the RNA2 coding sequence which add a NotI site at the 5' end and utilize the existing XbaI site at the 3' end. Fragment was cloned into the NotI/XbaI sites of the pVL1392 baculovirus expression vector.

```
p2BS(+)-wt   5' end                (-27 M13 Reverse Primer)

??    pBS                         RNA2         Start
5'   CC    AAGCT   CGAAATTAACCCTCACTAAA   GTAAACAATTCCAAGTTCAAAATGGTTAA  3'
3'   GG    TTCGA   CGTTTAATTGGGAGTGATTT   CATTTGTTAAGGTTCAAGGTTTTACCAATT 5'    (SEQ ID NO: 14)

p2BS(+)-wt   3' end                (-40 M13 Forward Primer)

RNA2                                                                  pBS
5' AAACCAGTTAAGTCAACAGACTAAGG TCTAGA GGATCCCCGGGTACCGAGCTCG AATTCGCCCTATAGTGAGTCGTATTACAATTCACTGGC 3'
3' TTTGGTCAATTCAGTTGTCTGATTCC AGATCT CCTAGGGGCCCATGGCTCGAGC TTAAGCGGGATATCACTCAGCATAATGTTAAGTGACCG 5'
                              XbaI    BamHI SmaI KpnI
                                             ??                              (SEQ ID NO: 15)
``` pVL1392:RNA2 DNA Sequence (PCR Primer sequences highlighted with lines):

```
       pVL1392              NotI              RNA2 5'                              RNA2 3'                  XbaI      pVL1392
5'  TCGGGCGCGGATCAGATCTGCA  GC GGCCGC  GTAAACAATTCCAAGTTCAAAATGGTTA--AGTCAACAGACTAAGG  T CTAGA  GGTACCCGGGATCC  3'
3'  AGCCCGCGCCTAGTCTAGACGT  CG CCGGCG  CATTTGTTAAGGTTCAAGGTTTTACCAAT--TCAGTTGTCTGATTCC  A GATC T  CCATGGGCCCTAGG  5'

(SEQ ID NO: 26)
```

FIG. 9

Primers For Subcloning RNA2 Constructs into pVL1392

5' NotI/RNA2 Primer (NT-RNA2)

NotI
5'  CA  GCGGCCGC  <u>GTA AAC AAT TCC AAG TTC CAA AAT GG</u>  3'  (36 mer, 26 underlined bases match template DNA)

(SEQ ID NO: 27)

3' XbaI/RNA2 Primer (RNA2-X)

XbaI
5'  <u>CC</u>  <u>TCTAGA</u>  CCT TAG TCT GTT GAC  3'  (23 mer, all bases match template DNA)

(SEQ ID NO: 28)

Primers as synthesized

(NT-RNA2, 36 mer)

5'  CAG CGG CCG CGT AAA CAA
    TTC CAA GTT CCA AAA TGG  3'  (SEQ ID NO: 27)

(RNA2-X, 23 mer)

5'  CCT CTA GAC CTT AGT CTG TTG AC  3'  (SEQ ID NO: 28)

FIG. 10 p2BS(+)-RNA2:HBV Constructs. Used oligonucleotide-mediated mutagenesis to insert coding sequences for HBV epitopes between RNA 2 amino acid residues 207 & 208.

RNA2 Peptide And Coding Sequence:

```
      CCG  GTT  GCA  ACA  GAT.......Peptide........ CCA  GCC  ACC  AGT  TCG     (CODING)
      GGC  CAA  CGT  TGT  CTA....Insertion Site.... GGT  CGG  TGG  TCA  AGC    (TEMPLATE)
203    P    V    A    T    D                         P    A    T    S    S    (AA SEQUENCE)     (SEQ ID NO:  16)
```

PreS2 132-145 Peptide And Coding Sequence:

```
132                                                          145
CAA  GAC  CCT  AGA  GTT  AGA  GGA  CTA  TAC  TTC  CCT  GCA  GGA  GGA
 Q    D    P    R    V    R    G    L    Y    F    P    A    G    G      (SEQ ID NO:  29)
```

RNA2:PRES2 132-145 Peptide And Coding Sequence:

```
3'  CCG GTT GCA ACA GAT..CAA GAC CCT AGA GTT AGA GGA CTA TAC TTC CCT GCA GGA GGA..CCA GCC ACC AGT TCG
5'  GGC CAA CGT TGT CTA..GTT CTG GGA TCT CAA TCT CCT GAT ATG AAG GGA CGT CCT CCT..GGT CGG TGG TCA AGC
     P   V   A   T   D    Q   D   P   R   V   R   G   L   Y   F   P   A   G   G    P   A   T   S   S
                                                                                          (SEQ ID NO: 30)
```

HBs 178-204 Peptide And Coding Sequence:

```
178                                                                                                  204
AAA CAA GCA GGA TTC TTC CTG CTG ACA AGA ATA CTG ACG ATA CCT CAA AGC CTG GAC AGC TGG TGG ACA AGC CTG AAC TTC
 L   Q   A   G   F   F   L   L   T   R   I   L   T   I   P   Q   S   L   D   S   W   W   T   S   L   N   F
                                                                                          (SEQ ID NO: 31)
```

RNA2:HBs 178-204 Peptide And Coding Sequence:

```
3'  CCG  GTT  GCA  ACA  GAT...
5'  GGC  CAA  CGT  TGT  CTA...
     P    V    A    T    D

AAA CAA GCA GGA TTC TTC CTG CTG ACA AGA ATA CTG ACG ATA CCT CAA AGC CTG GAC AGC TGG TGG ACA AGC CTG AAC TTC ...
TTT GTT CGT CCT AAG AAG GAC GAC TGT TCT TAT GAC TGC TAT GGA GTT TCG GAC CTG TCG ACC ACC TGT TCG GAC TTG AAG
 L   Q   A   G   F   F   L   L   T   R   I   L   T   I   P   Q   S   L   D   S   W   W   T   S   L   N   F

CCA  GCC  ACC  AGT  TCG
        GGT  CGG  TGG  TCA  AGC
         P    A    T    S    S      (SEQ ID NO: 32)
```

FIG. 11

Construction of a Functional RNA2:CSP Fusion

RNA2 Peptide And Coding Sequence:

```
    GGC CAA CGT TGT C

The mutagenic primer (CSP-P) is therefore:

5' CGA ACT GGT GGC TGG ...

ATT AGC AGA GCC AGG CTT TAT TCT AAC TTG TAT ...

ACC ATT TCC ACA AGT TAC ACT ACA TGG GGA CCA TTC ...

ATC TGT TGC AAC CGG 3'  (99 mer)　　　　(SEQ ID NO: 35)

The hybridization primer (CSP-H) is:

5' ACC ATT TCC ACA AGT TAC ACT ACA TGG GGA CCA  3'

(SEQ ID NO: 36)

Designed Primers.:

(CSP-P, 99 mer)

5' CGA ACT GGT GGC TGG ATT AGC
   AGA GCC AGG CTT TAT TCT AAC
   TTG TAT ACC ATT TCC ACA AGT
   TAC ACT ACA TGG GGA CCA TTC
   ATC TGT TGC AAC CGG　　　3'　　　　(SEQ ID NO: 35)

(CSP-H, 33 mer)

5' ACC ATT TCC ACA AGT TAC ACT
   ACA TGG GGA CCA　　　3'　　　　(SEQ ID NO: 36)

FIG. 12 (cont.)

RNA2 Sequencing Primers:

RNA2-S150 (20 mer)

5'   CCT CGT GCG ATT ACG TCG GC   3'         (SEQ ID NO: 37)

RNA2-S335 (20 mer)

5'   AGC TGA TAG ATT GAT TGA GG   3'         (SEQ ID NO: 38)

RNA2-S560 (20 mer)

5'   TCG ACG TTG GGT AAA TAC CC   3'         (SEQ ID NO: 39)

RNA2-S830 (20 mer)

5'   CCA AGG GAC ACA TTA GCA GG   3'         (SEQ ID NO: 40)

RNA2-S1010 (20 mer)

5'   TGG TAT AAC ATG GCG TTT GG   3'         (SEQ ID NO: 41)

RNA2-S1220 (20 mer)

5'   GCT GAC AGT CCA CTA ATA CC   3'         (SEQ ID NO: 42)

RNA2-S1160R (20 mer)

5'   GCT GCT GCA AGC AAC ATT CC   3'         (SEQ ID NO: 43)

Other Sequencing Primers:

pQE-S (22 mer)   Type III/IV pQE sequencing primer.

5'   CAC AGA ATT CAT TAA AGA GGA G   3'      (SEQ ID NO: 44)

FIG. 13

RECOMBINANT NODAVIRUS COMPOSITIONS AND METHODS

FIELD OF THE INVENTION

This invention relates to chimeric nodavirus related proteins such as antigenic peptides, and uses thereof. This invention also relates to virus-like particles comprising chimeric nodavirus related proteins and uses thereof.

BACKGROUND OF THE INVENTION

The immune system has several different mechanisms for dealing with pathogens in the system (Parker, D. C. 1993. *Annu. Rev. Immunol.* 11:331–360; *Clinical Immunology: Principles and Practice.* Vols. 1 and 2. eds (Fleisher et al. 1996. *Mosby-Year Book, Inc.* New York, N.Y.). The first step in the immune response is the activation of a special subclass of T lymphocytes called helper T cells. Macrophages present fragments of foreign proteins, or antigens, on their surfaces. Recognition of these antigens by specialized receptors found on helper T cells then initiates the two responses: a cell-mediated immune response and a humoral immune response.

The cell-mediated response involves principally the stimulation of another subclass of T lymphocytes called cytotoxic T lymphocytes (CTLs) that recognize and destroy infected cells. HLA class-I restricted molecules bind to peptides that have been processed intracellularly and enable CD8+T cells to eliminate intracellular viruses. CTLs are the second line of immune defense since the humoral response generates antibodies that may be able to neutralize virus and decrease the number of infected cells from the original infection. The CD4+T (Th) cells often have a helper phenotype, which is measured by their ability to assist the humoral response. The cells function to facilitate the effector function of other cells, and while Th cells have limited antiviral activity, they play a major role in providing intermolecular cooperation with antibody-producing B cells (Vitetta et al. 1989. *Adv. Immunol.* 45:1; Hodes, R. J. p. 587 In: 1989. *Fundamental immunology, eds* Paul, W. E.).

The humoral response, on the other hand, involves the activation of the second major class of lymphocytes, the B cells, to produce circulating antibodies. Antibodies recognize and neutralize soluble antigens, and mark cells or viruses bearing antigens for destruction by phagocytic cells. The HLA class-II molecules present the exogenous antigenic peptides to the class-II restricted CD4+B cells. Antibodies serve as efficient means of reducing the viral infectivity by several mechanisms. The antibody response to surface antigens on an invading pathogen can be very strong, and the antibody may be able to decrease the titer of virus particles significantly. In addition, antibodies can alter the structural integrity of the invading pathogen through interaction with surface antigens, which can make the virus non-infectious. Neutralization of the pathogen can also occur by preventing interaction with the cellular receptor and/or preventing endocytosis into the cytoplasm (Ruggeri, F. M. and Greenberg, H. B. *J. Virol.* 1991;2211–2219)Dimmock, N.J. In: *Current Topics in microbiology and immunology.* 1993. Springer-Verlag: New York).

Development of effective vaccines has been one of the most decisive advances leading to the dramatic downward trend in incidence of viral diseases. Vaccination induces a "primed" state in the vaccinated subject so that, following exposure to an antigen, a rapid secondary immune response is generated leading to accelerated elimination of the organism and protection from clinical disease. Designing vaccines requires attention to the safety of the system as well as to the antigenicity and efficacy of the prophylaxis.

It has been known for some time that humoral and cell-mediated responses to antigens can be quite different. In general, B cell epitopes of antigens are longer, and are known as conformational epitopes. Conformational epitopes require the proper 3-dimensional structure for efficient recognition by antibodies (Elner et al. 1977. *J. Immunol.* 118:2053). In contrast, T cells usually recognize small linear epitopes based on sequential information. Since effective resistance to viral or bacterial infection requires the activities of both humoral and cellular components, it is important to optimize the presentation of antigens to both B and T cells.

Despite recent advances in epitope presentation systems, there is still a need in the art for a system that is genetically capable of expressing of B and T cell epitopes concurrently, as well as presenting these epitopes to the immune system in the proper context.

There is evidence that simultaneous expression of T and B cell epitopes on the same carrier system can enhance the antibody response through a cooperative mechanism between B and T cells. For example, enhanced B cell vaccines to Hepatitis B are possible by stimulating hepatitis B virus (HBV) envelope protein-specific B cells though a carrier system that mimics HBV (Chisari, F. V. 1995. pp. 29–60 In: *Annu. Rev. Immunol*). If this carrier, or mimic, carries Th cell epitopes, the subsequent processing of these Th epitopes can induce the proliferation of B cells. For example, the HBV clearance depends on a vigorous and polyclonal B cell and T cell response to the envelope, nucleocapsid, and polymerase antigens. While the antibody responses to the HBV nucleocapsid and polymerase antigens are not well understood, it is quite clear that the antibody response to HBV envelope antigen requires T-cell cooperation. Despite the need for the vigorous immune response necessary to clear HBV, the class-II restricted envelope-specific response is quite low in acute and chronic hepatitis. The processing of Th epitopes can induce the proliferation of B cells and anti-envelope antibodies. An efficient means of enhancing the cooperation between B and Th cells due to increasing the exposure of B and Th cell epitopes via a carrier system would likely result in disease remission in patients. There is evidence that enhanced B cell vaccines to Hepatitis B are possible by stimulating HBV envelope-specific B cells though a carrier system that mimics HBV by properly presenting HBV determinants to antigen presenting cells (APCs).

While there is a substantial response of Class I-restricted CTL in acute cases, the CTL response to HBV is not easily detected in chronically infected patients who have been unable to clear virus. The ability to induce vigorous CTL expansion along with B and Th cell cooperation could have profound significance for the treatment of HBV infection as well as many other infectious diseases and cancer.

There have been remarkable advances made in vaccination strategies recently, yet there remains a need for improvement on existing strategies. Recombinant pathogenic viruses have often induced the strongest humoral and cell-mediated responses, but the issues of safety and potential interference with pre-existing immunity to the vectors have not made them an attractive system for continued use. Peptide vaccines have been shown to be relatively safe with a strong monofunctional immune response. Despite these advantages, they tend to be poorly immunogenic and have a limited ability to bind selectively to different MHC determinants found in genetically distinct populations of individuals. While it may be possible to produce numerous peptides for formulation into a single vaccine, such an undertaking presents a formidable task. Genetic immunization, or DNA vaccines, has shown promise, but has not shown the ability to target APCs and produce a broad polyclonal response. Despite these advances, the current technologies have not provided a system that was competent in the simultaneous expression of B and T cell epitopes that effectively prime B and T cells of the immune system.

In these non-limiting examples, genetically-engineered Nodaviral or specifically the Flock House Virus (FHV) chimeric coat protein constructs were made to include well-defined ligands within the insertion region as well as encapsidation of therapeutic genes or antisense.

Gene delivery or gene therapy can be defined as the delivery of a functional gene (for expression of a protein) or an antisense molecule (for blocking translation of a protein) to somatic cells. See, for example, U.S. Pat. No. 5,589,466 to Felgner et al. and U.S. Pat. No. 5,676,954 to Brigham. For reviews see Mitani, K, and Caskey, C. T. (1993) *TIBTECH* 11:162–166, Findeis, M. A. et al. (1993) *TIBTECH* 11:202–205; Friedmann, T. (1994) *TIG:* 10:210–214, Smith, C. (1994) *TIG:* 10:139–144; Karpati et al. (1996) *TIBS* 19:49–54; Calos, M. P. (1996) *TIG:* 12:463–466. Several gene delivery technologies that are being used to treat a variety of diseases and acquired and genetic disorders are summarized in Table 1.

TABLE 1

Comparison of Gene Delivery Technologies

| Vector | Insert Size | Integration | Transduction efficiency | Advantages | Disadvantages |
| --- | --- | --- | --- | --- | --- |
| Retrovirus | 8 kB | Yes | High | Stable transfection of dividing cells. | Infects only rapidly dividing cells. Can be oncogenic. |
| Adenovirus | 7.5 kB | No | High | Transfects nearly all cell types dividing or nondividing. | Transient expression triggers immune response, common human virus |
| Adeno Associated Virus (AAV) | 4 kB | Yes. (chr. 19) | High | Stable transfection. | Small insert size, integration poorly understood. Helper virus required. |
| Herpes Simplex Virus (HSV) | 20 kB | No | Low | Large insert size. Neuron specific. | Transient expression, potential to generate infectious HSV in humans |
| Vaccinia | 25 kB | No | High | Infects a variety of cells effectively. | Limited to non-smallpox vaccinated or immuno-compromised individuals. |
| Liposomes | 20 kB | No | N/A | Large insert size. | Transient expression is disadvantage combined with variable delivery. |
| Ballistic ("biollistic") Injection | 20 kB | No | N/A | Large insert size. | Requires exposed tissue. |
| Plasmid DNA Injection | 20 kB | No | N/A | Large insert size. | Poor delivery. Only sustained expression in muscle. |

Recombinant Flock House virus (FHV) proteins displaying viral antigens have been described (Tisminetzky, S. G. et al., *FEBS Lett.* 353:1–4 (1994); Scodeller, E. A., et al. *Vaccine,* 13:1233–1239 (1995); Buratti, E., et al., *J. Immunol. Methods,* 197:7–18 (1996); Schiappacassi, M., et al., *J. Virol. Methods,* 63:121–127 (1997); Buratti, E., et al., *Clin. Diagn. Lab. Immunol.,* 4:117–12 (1997). See also Baralle, F. E. et al., PCT Published Application WO 96/05293 (1996). These previous attempts suffer from difficulties in forming a virus-like particle due to the deletion of amino acid residues in one or more regions of the capsid protein, however.

What is needed are recombinant nodavirus related proteins that can incorporate heterologous peptides as long as 100 amino acid residues or larger yet still be capable of self-assembly into chimeric virus-like particles.

SUMMARY OF THE INVENTION

The present invention provides a chimeric protein which comprises a nodavirus capsid (or coat) protein free from any deletion, having a core structure constituted by anti-parallel beta barrels, and a heterologous peptide segment situated between a pair of strands of a beta barrel. A preferred chimeric protein is a Flock House virus capsid protein together with a heterologous peptide segment present in the capsid protein at a location between amino acid residue 205 and amino acid residue 209 from the amino terminus of the capsid protein. All amino acid residues normally present in the nodavirus capsid protein are retained. The amino acid sequence of the heterologous peptide segment is chosen from cell-specific targeting sequences such as B cell epitopes, T cell epitopes, and sequences targeting other cell types. The heterologous peptide segment can have a size of up to about 100 amino acid residues.

An embodiment of the present invention is a nodavirus system for delivery of a biologically active moiety, which system includes a chimeric capsid protein. The biologically active moiety can be a direct immunostimulant, an indirect immunostimulant, a gene encoding a direct immunostimulant, or a gene encoding an indirect immunostimulant. Chimeric proteins, as well as nodavirus particles, conjugated to an antigenic protein can also serve as effective immunostimulants or immunomodulators, and are useful for diagnostic as well as immunizing purposes.

In accordance with the present invention, the need for nonpathogenic vectors as described above has been satisfied by a novel viral-like based system that provides therapeutic compositions including vaccines, as well as diagnostic embodiments, such as diagnostic kits. Flock House virus (FHV) is one such nodavirus that can be used to genetically engineer virus-like particles carrying antigenic peptides on their surface. The basis for this system is centered on the remarkable functional versatility of the FHV capsid protein. Extensive computational chemical analysis of the high resolution atomic structure of FHV has led to the identification of a region in the capsid protein that is amenable to insertion of heterologous peptide segments without affecting assembly of the viral coat or capsid. The predictions from the structural and computational studies have been used to genetically construct FHV-like chimeric virus-like particles that contain well-defined antigenic determinants as inserted heterologous peptides. These inserted heterologous peptides include B cell epitopes that are presented on the surface of the carrier in the proper conformation to generate a humoral response. Other heterologous peptide segments, such as those containing T cell epitopes, have been expressed on the surface of such chimeric virus-like particles, producing a structure that generates a proliferative and CTL response. Heterologous peptide segments comprising contiguous B cell epitopes and T cell epitopes inserted to form chimeric proteins have demonstrated enhanced immunogenicity.

BRIEF DESCRIPTION OF THE DRAWINGS

In the Drawings,

FIG. 2 shows predicted the secondary structure that represent the encapsidation signal in RNA 2 of several nodaviruses.

FIG. 4 shows the p2BS(+)-wt sequence immediately flanking the RNA2 insert, determined by sequencing the ends of p2BS(+)-wt, p2BS(+)-RNA2:VSV-G #1, p2BS(+)-RNA2:BRSV #1.

FIG. 5 shows the sequence of p2BS(+)-RNA2:VSV-G constructs.

FIG. 6 shows the sequences of the RNA2:VSV-G mutagenic primer and the hybridization probe.

FIG. 7 shows the sequence of p2BS(+)-RNA2:BRSV constructs.

FIG. 8 shows the sequence of the RNA2:BRSV mutagenic primer.

FIG. 9 shows the scheme of the construction of the pVL1392-RNA2, pVL1392-RNA2:VSV-G & pVL1392-RNA2:BRSV baculovirus expression vectors.

FIG. 10 shows the sequences of primers For subcloning RNA2 constructs into pVL1392.

FIG. 11 shows the sequences of p2BS(+)-RNA2:HBV constructs.

FIG. 12 shows the scheme of the construction of the functional RNA2:CSP fusion construct.

FIG. 13 shows the sequences of RNA2 and other sequencing primers.

DETAILED DESCRIPTION OF PREFERRED EMBODIMENTS

The present invention uses members of the Nodaviridae virus family, commonly known as nodaviruses, such those listed in Table 2, below, to produce chimeric proteins capable of self-assembly into chimeric virus-like particles.

TABLE 2

| | Nodaviruses | |
|---|---|---|
| Member | Propagation in Cell Culture | Protein Expression Systems |
| Nodamura virus (NV) | BHK-21, mosquito cells | Baculovirus and *E. coli*. expression systems |
| Flock House virus (FHV) | *Drosophila* cells, Black | Baculovirus and *E. coli*. expression systems |
| Black Beetle virus (BBV) Boolarra virus (BoV) Gypsy moth virus (GMV) Manawatu virus (MwV) | Beetle cells, protoplasts | |

Suitable nodaviruses include Nodamura virus (NV), Flock House virus (FHV), Black Beetle virus (BBV), Boolarra virus (BoV), Gypsy moth virus (GMV), and Manawatu virus (MwV). A preferred nodavirus is the Flock House virus (FHV).

Figure 1:
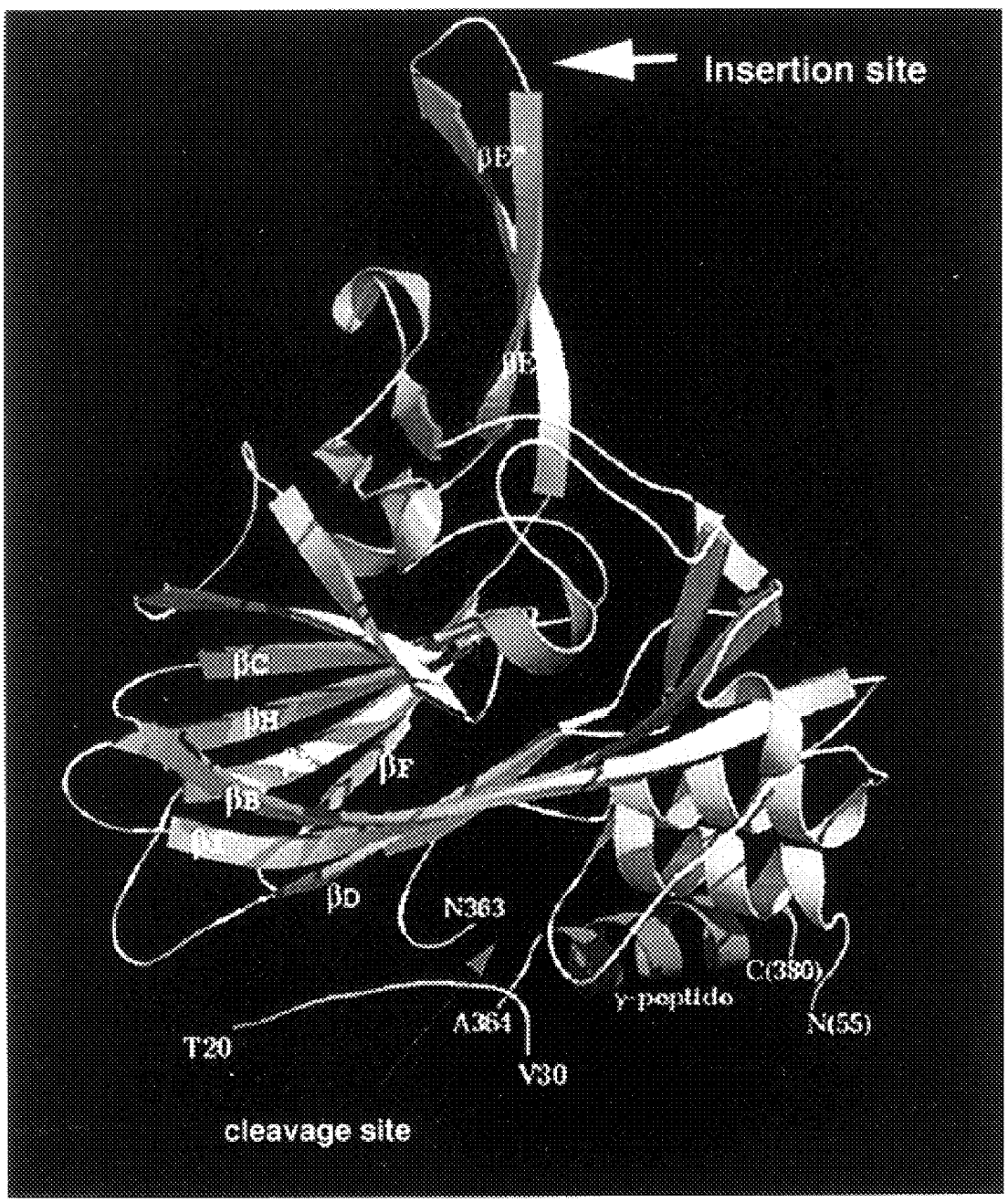
FIG. 1 shows the tertiary structure of the FHV coat protein subunit.
Figure 3:
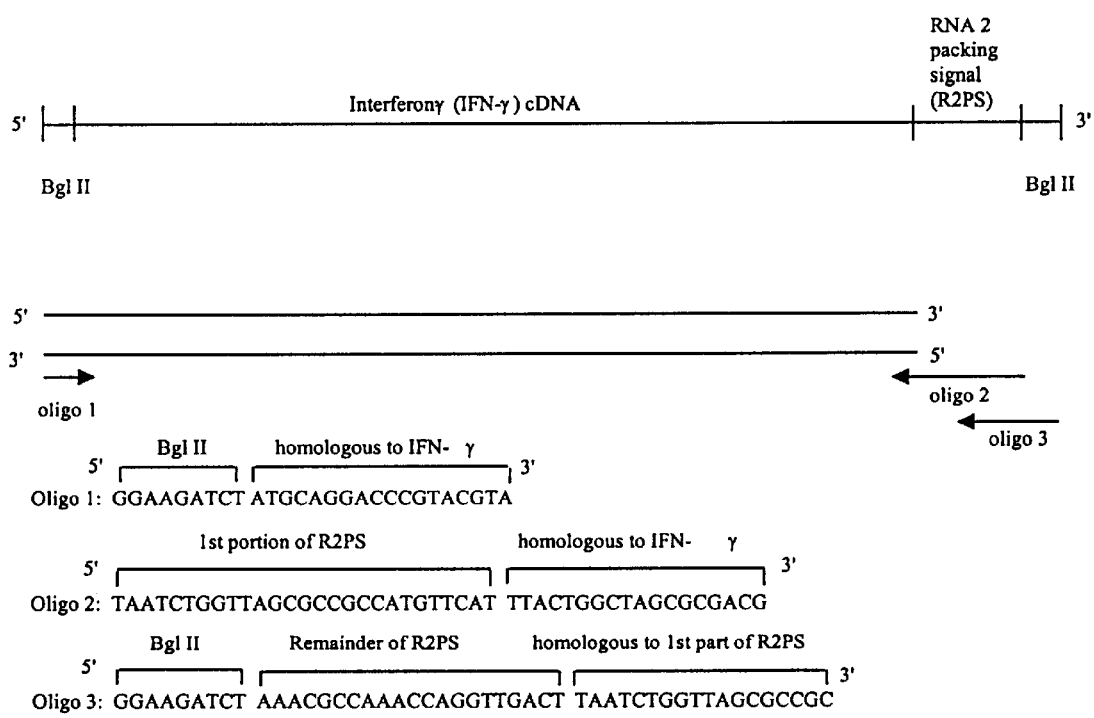
FIG. 3 shows the grafting of FHV encapsidation signal to the end of a gene of therapeutic interest, human interferon-γ.
Figure 14A:
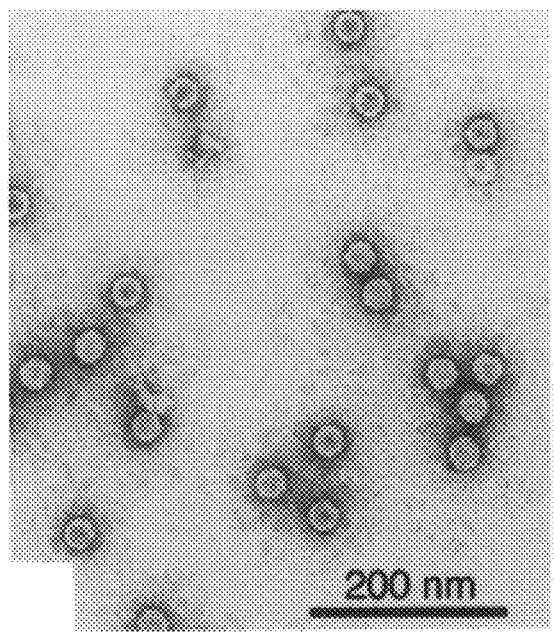
FIG. 14 shows an electron micrograph of chimeric FHV particles with an VSV epitope inserted into the coat protein. An epitope was derived from Vesicular Stomatitis Virus (VSV) to generate a FHV:VSV chimeric particle. The epitope TyrThrAspIleGluMetAsnArgLeuGlyLys (SEQ ID NO:1) was inserted into the FHV coat protein gene and introduced into the baculovirus expression system. Panel A shows chimeric virus-like particles that were isolated from baculovirus-infected *S. frugiperda* cells and subjected to electron microscopy using standard negative staining conditions (Magnification×39,000). Note the icosahedral shape of the stable chimeric virions. Panel B shows chimeric FHV:VSV chimeric particles were isolated from baculovirus-infected *S. frugiperda* cells and subjected to immuno-electron microscopy (Magnification×39,000). The FHV:VSV chimeric particles are decorated with the monoclonal antibody P5D4 (MAb P5D4) against the aforementioned 11-residue VSV epitope (SEQ ID NO:1) which was inserted into the FHV coat protein. MAb P5D4 is of subtype $IgG_1k$ and can be seen binding to the VSV epitope, which gives a dark halo-like appearance to the chimeric particles. The antibody also induces mild aggregation due to the presence of IgG.
Figure 14B:
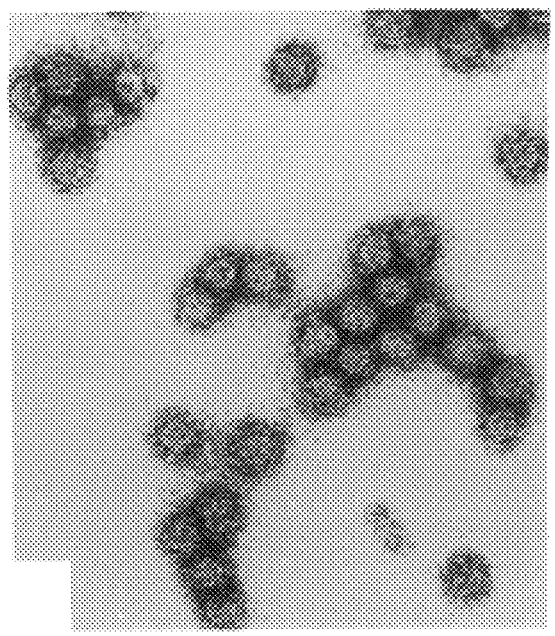

The structure of the Flock House virus coat protein, also known as the capsid protein, is shown in FIG. 1. The amino acid residue sequence, left-to-right in the direction from the amino or N-terminus to the carboxy or C-terminus of this protein is as follows:

```
                                             (SEQ ID NO:10)
     Met Val Asn Asn Asn Arg Pro Arg Arg Glu

Arg Ala Glu Arg Val Val Val Thr Thr Thr

Glu Thr Ala Pro Val Pro Glu Glu Asn Val

Pro Arg Asn Gly Arg Arg Arg Arg Asn Arg

Thr Arg Arg Asn Arg Arg Arg Val Arg Gly

Met Asn Met Ala Ala Leu Thr Arg Leu Ser

Gln Pro Gly Leu Ala Phe Leu Lys Cys Ala

Phe Ala Pro Pro Asp Phe Asn Thr Asp Pro

Gly Lys Gly Ile Pro Asp Arg Phe Glu Gly

Lys Val Val Ser Arg Lys Asp Val Leu Asn

Gln Ser Ile Ser Phe Thr Ala Gly Gln Asp

Thr Phe Ile Leu Ile Ala Pro Thr Pro Gly

Val Ala Tyr Trp Ser Ala Ser Val Pro Arg
```

-continued

```
Gly Thr Phe Pro Thr Ser Ala Thr Thr Phe

Asn Pro Val Asn Tyr Pro Gly Phe Thr Ser

Met Phe Gly Thr Thr Ser Thr Ser Arg Ser

Asp Gln Val Ser Ser Phe Arg Tyr Ala Ser

Met Asn Val Gly Ile Tyr Pro Thr Ser Asn

Leu Met Gln Phe Ala Gly Ser Ile Thr Val

Trp Lys Cys Pro Val Lys Leu Ser Thr Val

Gln Phe Pro Val Ala Thr Asp Pro Ala Thr

Ser Ser Leu Val His Thr Leu Val Gly Leu

Asp Gly Val Leu Ala Val Gly Pro Asp Asn

Phe Ser Glu Ser Phe Ile Lys Gly Val Phe

Ser Gln Ser Ala Cys Asn Glu Pro Asp Phe

Glu Phe Asn Asp Ile Leu Glu Gly Ile Gln

Thr Leu Pro Pro Ala Asn Val Ser Leu Gly

Ser Thr Gly Gln Pro Phe Thr Met Asp Ser

Gly Ala Glu Ala Thr Ser Gly Val Val Gly

Trp Gly Asn Met Asp Thr Ile Val Ile Arg

Val Ser Ala Pro Glu Gly Ala Val Asn Ser

Ala Ile Leu Lys Ala Trp Ser Cys Ile Glu

Tyr Arg Pro Asn Pro Asn Ala Met Leu Tyr

Gln Phe Gly His Asp Ser Pro Pro Leu Asp

Glu Val Ala Leu Gln Glu Tyr Arg Thr Val

Ala Arg Ser Leu Pro Val Ala Val Ile Ala

Ala Gln Asn Ala Ser Met Trp Glu Arg Val

Lys Ser Ile Ile Lys Ser Ser Leu Ala Ala

Ala Ser Asn Ile Pro Gly Pro Ile Gly Val

Ala Ala Ser Gly Ile Ser Gly Leu Ser Ala

Leu Phe Glu Gly Phe Gly Phe
```

The nucleotide sequence for the foregoing amino acid residue sequence is known, and is described by Dasgupta, R. et al., Nucleic Acids Res. 17(18):7525–7526 (1989).

The core of the structure is made up of eight stranded anti-parallel beta-barrels, as seen in many other viral capsid proteins. The helical domain is made up of 3 alpha-helices, formed by the polypeptide chain located sequentially, 'N' and 'C' terminal to the beta-barrel. The helix is the gamma-peptide, one of the cleavage products. A region between amino acids 205–209 from the "N" terminus forms a loop that is exposed on the exterior surface of the assembled capsid. The formed loop is between the βE-βF strands of a beta barrel. The insertion itself forms a pair of β-strands, βE'-β", with a short loop therebetween, as can be seen in FIG. 1.

The FHV genome contained within the capsid includes two messenger-sense RNA molecules, RNA 1 and RNA 2 (Schneemann, A., et al. 1993. In W. Doerfler and P. Bhm (eds.), Viral Strategies, Verlag Chemie, Weinheim, Germany. p. 167–176). RNA 1 (3.1 kb) directs synthesis of protein A (102 kDa) the putative RNA-dependent RNA polymerase (Fisher, A. J. and J. E. Johnson. 1993. Nature (London) 361:176–179). RNA 2 (1.4 kb) encodes protein alpha (43 kDa), the precursor of the coat protein (Gallagher, T. M. and R. R. Rueckert. 1988. J. Virol. 62:3399–3406). In addition to the genomic RNAS, infected cells also contain a subgenomic RNA 3 (0.4 kb) derived from the 3' end of RNA 1. It encodes protein B (10 kDa), whose function is to modulate replication (Ball, L. A. (1994) PNAS 91:12443–12447; Ball, L. A. (1995) J. Virol. 69:720–727).

A specific region of FHV RNA 2 (bases 186–217) has a predicted stem-loop structure (FIG. 2), which serves as the packaging signal for in vivo encapsidation of RNA 2 (Zhong, W., Dasgupta, R., and Rueckert, R. 1992. Proc. Natl. Acad. Sci. USA 89:11146–11150). Similar regions of the other Nodaviral RNA 2 sequences are also shown in FIG. 2 and serve an identical function. The initial step is believed to involve the formation of a nucleating complex, in which a coat protein substructure interacts with this encapsidation signal on the viral RNA. The initiation complex may then be propagated into a spherical particle by addition of coat protein subunits, which are guided into the growing shell by binding to the viral RNA.

Flock House virus (FHV) can be grown to high titers in Drosophila cell culture with synthesis of proteins A and B peaking at about 5 hours and 8 hours, respectively (Schneemann, A., et al. 1993. In W. Doerfler and P. Bhm (eds.), Viral Strategies, Verlag Chemie, Weinheim, Germany. p. 167–176). In contrast, synthesis of protein alpha remains low during the first 12 hours but rises rapidly thereafter with peak production at about 15 hours. The newly synthesized alpha chains are assembled within minutes into labile precursor particles, called provirions. Provirions contain 180 alpha subunits, arranged with icosahedral symmetry, as well as a copy of each of the genomic RNA molecules. The assembly process triggers an autoproteolytic reaction in the 407 amino acid alpha chain which results in cleavage between asparagine 363 and alanine 364 (Hosur, M. V. et al. 1987. Proteins: Struc. Funct. Genet. 2:167–176; Fisher, A. J. and J. E. Johnson. 1993. Nature (London) 361:176–179).

The newly formed polypeptides, beta (38 kDa, 363 amino acids) and gamma (5 kDa, 44 amino acids), remain associated with the mature virion.

Following injection of wild-type FHV, antibody formation occurs without symptoms or disease in pigs, adult mice, rabbits, guinea pigs, Syrian hamsters, and chickens. In addition, there is no cytopathology in mammalian cell culture lines including primate kidney and human amino cells (Hendry, D. A. 1991. In Viruses of Invertebrates (ed. E. Kurstak) Marcel Dekker, Inc.: New York).

The structure of FHV was solved to atomic resolution and shows that the viral capsid is composed of 60 triangular units, which consist of three identical polypeptides related by icosahedral symmetry (Hosur, M. V. et al., 1987. Struc. Funct. Genet. 2:167–176). All three subunits, designated A, B and C, contain a central beta-barrel motif similar to that observed in many other virus structures (Rossmann, M. G. and J. E. Johnson. 1989. Ann. Rev. Biochem. 58:533–573). The exterior surface consists of elaborate loops between the beta-strands and the inner surface is made up of helical domains from the amino- and carboxy-terminal ends of the protein. The helical domain formed by the amino-terminal end of the protein is only visible for the C subunits, in which amino acid residues 20 through 30 constitute an ordered peptide "arm". In the A and B subunits, the amino terminal-end is disordered and not visible in the electron density map. This variation results in a significant difference in the subunit contacts across the icosahedral twofold and quasi-twofold axes. While the interaction between the protein subunits across the quasi-twofold axes ($A/A_2$ and $C/B_5$) are bent, the interactions across the twofold axes ($C/B_2$ and $C_2/B$ contacts are flat. This is because the peptide arm in the C subunits folds into the hinge between the subunits, preventing them from forming the dihedral angle seen at the quasi-twofold axes. In addition, the flat joint at the twofold axes is stabilized by a segment of genomic RNA that forms a wedge between the $C/C_2$ joints, but not the $A/B_5$ joints.

The alpha protein cleavage site is located deep inside the virion near the RNA core, explaining its inaccessibility to proteinase inhibitors and virus precipitating antibodies. The cleavage product gamma (carboxy-terminal residues 364–407) is located in the particle interior and forms an amphipathic-helix. At the twofold axes of symmetry, the gamma helices interact with the ordered duplex RNA whereas at the fivefold axes they form a pentameric helical bundle that is stabilized by interactions among the hydrophilic surfaces of the helices (Cheng, H. R. et al. 1994. *Structure* 2:271–282).

Identification of the Insertion Site of Foreign Sequences into the FHV Genome

Computational chemical analysis of the high resolution atomic structure of FHV and molecular genetic analysis of the genome has led to the identification of regions in the coat protein subunits that are amenable to insertional mutagenesis of up to approximately 100 amino acids without affecting viral assembly. This region of the coat protein encompasses amino acids 205–209 and is a loop that is well exposed on the virus surface (FIG. 1). Corresponding loops can be found on the surface of each of the other nodavirus family members.

In accordance with a preferred embodiment of the present invention, a specific location within the FHV coat protein gene is amenable to insertion of foreign sequences up to about 300 base pairs (up to about 100 amino acid residues), which does not interrupt the viral assembly process. That location is between adjacent beta barrels of the protein core structure as described hereinabove.

This invention provides methods of producing the chimeric FHV-like proteins as well as diagnostic and therapeutic uses of the proteins.

FHV-like multivalent chimeric proteins together with the inserted heterologous peptide segment provide more than one cell specific signal. For example, both Bovine Respiratory Syncytial virus (BRSV) F protein comprises both a B cell epitope and a T cell epitope (Table 3). Such multivalent chimeric proteins can be produced in high titers, preferably when introduced into the baculovirus expression system.

Multivalent chimeric virus-like particles in turn can be produced by the expression and assembly of a multivalent chimeric protein in the baculovirus expression system. Alternatively, multivalent chimeric virus-like particles comprising at least two chimeric proteins can be co-expressed in a baculovirus and assembled. Each of the co-expressed chimeric proteins contains an inserted heterologous peptide segment that provides at least one cell specific signal.

The maximum size of a peptide encoding sequence is about 300 base pairs, which results in the insertion of a foreign or heterologous peptide segment of about 100 amino acids. The sequence composition of this region of the chimeric coat protein gene is:

5' CGAACTGGTGGCTGG . . . (n)$_{-300}$ . . . ATCTGT-TGCAACCGG 3' (Nucleic acid residues 1–15 and 49–63 of SEQ ID NO 20)

where the 15 bases at the 5' and 3' ends of the oligonucleotide are complementary to bases 629–643 and 644–658 of the RNA 2 message strand sequence, and (n)$_{-300}$ is a stretch of about 300 nucleotides that encode the peptide segment sequence to be expressed.

Since there are 180 copies of the coat protein present in any one particle, the maximum theoretical number "N" of different epitopes that may be presented on the surface of one particle is $N \leq 180$. In practice however, it may be technically advantageous to limit the number of different epitopes present on the surface of any one particle to $N \leq 30$ (i.e., to no more than six different epitopes on any one particle) so as to avoid reduction of the molecular mass of any one distinct epitope to a value below any minimum threshold necessary to induce a sufficient immune response.

There do not appear to be any restrictions other than size for insertion, although post-translational modifications in the system may affect antigenicity. While the coat protein does not have glycosylation signals or disulfide bonds, insect cell lines in which the virus can be propagated, such as those in which baculovirus is expressed, do post-translationally modify proteins in a very similar manner to that seen in mammals. In the non-limiting examples given below, epitopes were chosen that did not have glycosylation sites or cysteines where disulfide bonds might be expected to form. Nonetheless, this system is also effective for epitopes who require such post-translational changes necessary for proper antigenicity. In addition, bacterial expression systems may be used to produce the chimeras where epitopes have been inserted, which do not require post-translational changes inasmuch as bacterial systems are not capable of post-translational modifications of proteins.

The molecular construction of the chimeric coat protein genes can be achieved by single-stranded plasmid DNA oligonucleotide-mediated mutagenesis (Kunkel, T. A. 1985. *PNAS* 82:488–492; Kunkel, T. A., Roberts, J. D., and Zakour, R. A. 1987 *Meth. Enzymol.* 154:367–382). This scheme involves a DNA sequence that can be specifically altered by synthesizing the desired sequence change within an oligonucleotide, and then converting this into a biologically active circular DNA strand by using the oligonucleotide to prime in vitro synthesis on a single-stranded circular DNA template.

As stated hereinabove, given that the limitations of the single-step, single-stranded plasmid DNA oligonucleotide-mediated mutagenesis become apparent when attempting to generate primers much longer than about 100 bases, other molecular methods can be employed by a person skilled in the art of molecular genetics to generate insertions larger than about 100 bases.

PCR-based techniques can be used that require three primers: two flanking primers, which anneal to regions upstream and downstream of the mutation site, and one mutagenic primer. The upstream and downstream primers is kept constant while the mutagenic primer changes with each mutagenesis. Modifications allow substitution, deletion and insertional mutagenesis. The megaprimer method of site directed mutagenesis has been successfully performed with megaprimers greater than 800 bp in length (Sarkar, G. and S. S. Sommer. 1990. *BioTechniques* 8:404–407; Picard, V. E. et al. 1994. *Nucleic Acids Res.* 22:2587–2591). To place mutations in this region of the cDNA clone of the FHV coat protein requires a megaprimer containing maximally about 700 base pairs.

For insertional mutagenesis of genes, a PCR-based technique can be used that requires four primers: two flanking primers at the 5' and 3' ends of the gene with suitable restriction sites engineered in for priming, which anneal to regions upstream and downstream of the mutation site, and two mutagenic primers. The upstream and downstream primers are kept constant while the mutagenic primers change with each mutagenesis. Approximately 15–20 bases of each mutagenic primer is complementary to the wild-type sequence, and the remainder represents the insertion sequence.

In this particular scheme, the 5' PCR primer complementary to the FHV wild type sequence is placed in a reaction with a 3' primer that has 15–20 bases complementary to the FHV wild-type sequence directly proximal to the insertion sequence in accordance with molecular biology principles. In a second reaction, a 3' PCR primer is used that is complementary to the wild-type sequence directly distal to the complement of the insertion sequence in accordance with molecular biology principles. These two separate PCR amplifications are performed, and the resulting PCR products are purified and subjected to a third round of PCR. In this third round of PCR, both PCR products are combined along with the 5' and 3' flanking primers that are complementary to wild-type sequence. No mutagenic primers are used in this third round of PCR. In the initial cycles of this final PCR, the insertion sequence and its complement anneal and create a full-length chimeric template, which is amplified in subsequent rounds of PCR. In all reactions, the following conditions are typical:

Cycle 1: Denature at 94 degrees Celsius for three minutes.
Cycles 2–30: Denature at 94 degrees Celsius for one minute and thirty seconds.
Anneal at 53 degrees Celsius for one minute.
Extend at 72 degrees Celsius for two minutes.
Cycle 31: Extend at 72 degrees Celsius for seven minutes.
Cycle 32: Hold at 4 degrees Celsius until samples are purified and analyzed.

To insure that the sequence changes generated during PCR are limited to those introduced by the mutagenic primer, a thermostable DNA polymerase that has proofreading capabilities, e.g. Pfu polymerase, is used (Marini, F. III. et al. 1993. *Nucleic Acids Res.* 21:2277–2278). Such polymerases have the additional advantage that they lack terminal transferase activity which usually results in addition of non-templated bases at the 3' end of amplified DNA products. The number of PCR cycles is kept to a minimum to further decrease the possibility of introducing unwanted sequence changes. The final PCR product is then purified, subcloned and tested for the presence of the desired mutation.

Other methods of PCR-based insertional mutagenesis can be employed by those skilled in the art of molecular genetics to create the chimeras.

The Preferred Expression System: Baculovirus Expression System

FHV-like particles were generated by expressing the FHV coat protein chimeric genes in the baculovirus expression system (Vlak, J .M. and Keus, R. J. A. 1990. In *Viral Vaccines*. Wiley-Liss, Inc., New York. pp. 91–128.; O'Reilly, D. R., Miller, L. K., and Luckow, V. A. 1992. *Baculovirus Expression Vectors: A Laboratory Manual*. W. H. Freemnan and Co., New York). This allows for the large-scale production of chimeric particles that are purified biochemically and prepared for testing in vitro and in vivo as suitability for vaccines. Typical preparations yield 1–2 mg of particles per $6\times10^9$ infected Sf9 cells. Yields from T. ni. cells can exceed 50 mg per $10^9$ infected cells.

cDNAs of FHV RNA 2 encoding the chimeric coat protein alpha are placed under control of the polyhedron promoter and inserted into the baculovirus genome by homologous recombination. The mRNAs of the coat protein expressed in the heterologous system are considerably longer than the 1,400 bases comprising authentic FHV RNA 2. This is because the sequence of RNA 2 lacks eukaryotic transcription termination and polyadenylation signals, which are provided by the flanking polyhedron sequences. The final wild-type transcripts are about 2,100 bases long, including a poly(A) tail, which is not present in authentic FHV RNA 2. This system has been extensively tested to determine whether coat protein expressed in the absence of RNA 1 and in the presence of a significantly larger RNA 2 would be able to assemble into particles suitable for crystallographic analyses. As expected, the capsid proteins spontaneously assemble into virus-like particles that even package the mRNA of the coat protein. These studies also demonstrate that RNA 1, which is required for replication of the FHV genome, is dispensable for virion assembly.

Therefore, using the baculovirus expression system to produce FHV chimeras it is not necessary to utilize RNA 1. In this case a RNA2:VSV chimeric coat protein was constructed and put it into the baculovirus expression system. Therefore the particles package only RNA2:VSV chimeric RNA.

For purposes of clarity, the term FHV:VSV or FHV:BRSV BRSV will be used to represent the chimera RNA2:VSV or RNA2:BRSV constructs.

As discussed herein, an optimal method of generating chimeric coat protein genes and the resulting particles is by utilizing the baculovirus expression system. This obviates the need to provide the FHV replicase since the replication machinery is provided by the baculovirus system.

Other methods may be employed to generate FHV-like chimeric particles. For examples, the chimeric proteins can be produced by the generation of heterologous capsid protein RNA followed by the inoculation of plant systems or by transfecting many other cell lines with the RNA. These alternate systems depend on the ability of FHV to be able to replicate, which may be hindered to some degree in these alternate systems since the insertion site may be close to the putative receptor binding site, which has not been conclusively determined to date.

Alternatively, specialized plasmids containing copies of the FHV chimeric capsid protein cDNA can be constructed in a similar method as discussed herein and used to make transcripts that direct their own replication. By incorporating a phage polymerase promoter in the upstream primer, the PCR-generated DNAs can be used directly as templates for in vitro transcription of RNA without prior subcloning. This method generates high titers of chimeric nodavirus proteins providing that the replicase transcript has a normal level of activity and the particles can replicate in the particular host cell through binding to cellular receptors.

In these non-limiting examples, genetically-engineered FHV chimeric coat protein constructs were made to include well-defined epitopes from the viruses listed in Table 3, below.

TABLE 3

Chimeric Coat Protein Constructs

| Viral Epitope | Reference |
|---|---|
| Vesicular Stomatitis virus (VSV) G glycoprotein Viral strain: ts-045 VSV Indiana serotype B cell epitope TyrThrAspIleGluMetAsnArgLeuGlyLys (SEQ ID NO:1) | Kreis, T. E. (1986) EMBO J. 5: 931–941 Kolodziej, P. A. & Young, R. A., (1991) Methods Enzymol. 194: 508–519 |
| Bovine Respiratory Syncytial virus (BRSV) F protein Viral strain: RB94 Contiguous B and T cell epitopes AspLysGluLeuLeuProLysValAsnAsnHisAspCysGlnIleSer AsnIleAlaThrValIleGluPheGlnGln (SEQ ID NO:2) | Walravens et. al., (1990) J. Gen Virol. 71: 3009–3014 Bourgeois et al. (1991) J. Gen. Virol. 72: 1051–1058 |
| Human Respiratory Syncytial virus (RSV) F protein Viral strain: RSS-2 (subtype A) Contiguous B and T cell epitopes AspLysGlnLeuLeuProIleValAsnLysGlnSerCysSerIleSerAsn IleGluThrValIleGluPheGlnGln (SEQ ID NO:3) | Walravens et. al., (1990) J. Gen Virol. 71: 3009–3014 Bourgeois et al. (1991) J. Gen. Virol. 72: 1051–1058 |
| Human Respiratory Syncytial virus (RSV) F protein Viral strain: 18537 (subtype B) Contiguous B and T cell epitopes AspLysArgLeuLeuProIleValAsnGlnGlnSerCysArgIleSer AsnIleGlnThrValIleGluPheGlnGln (SEQ ID NO:4) | Walravens et. al., (1990) J. Gen Virol. 71: 3009–3014 Bourgeois et al. (1991) J. Gen. Virol. 72: 1051–1058 |
| Human Respiratory Syncytial virus (RSV) Bovine Respiratory Syncytial virus (BRSV) F protein Viral strains: RSS-2 (subtype A) (RSV) 18537 (subtype B) (RSV) RSS-2 (subtype A) (BRSV) T cell epitope PheProSerAspGluPhe [100% sequence conservation] (SEQ ID NO:5) | Walravens et. al., (1990) J. Gen Virol. 71: 3009–3014 Bourgeois et al. (1991) J. Gen. Virol. 72: 1051–1058 |
| Hepatitis B Virus (HBV) preS2 Residues 132–145 B cell epitope GlnAspProArgValArgGlyLeuTyrPheProAlaGlyGly (SEQ ID NO:6) *double chimera made with epitope below | Neurath, A. R., et al. 1986. Vaccine 4: 35. Itoh, Y., et al 1986. Proc. Natl. Acad. Sci. USA. 83: 9174. |
| Hepatitis B Virus (HBV) HBsAg residues 178–204 overlapping Th and CTL epitopes LeuGlnAlaGlyPhePheLeuLeuThrArgIleLeuThrIleProGln SerLeuAspSerTrpTrpThrSerLeuAsnPhe (SEQ ID NO:7) | Franco, A., Guidotti, L. G., Hobbs, M. V., Pasquetto, V., and Chisari, F. V. 1997. J. Immunol. in press. Greenstein, J. L., et al. 1992. J. Immunol. 148: 3970. |

The nodavirus system of the present invention has also been developed to be a gene delivery vehicle capable of target cell-specific delivery of therapeutic mRNA molecules. Briefly, ligands are inserted into the same region of the coat protein gene as previously indicated and using the same criteria and parameters, which creates chimeric particles with target cell-specificity.

Grafting this packaging signal onto genes of therapeutic interest causes hybrid RNA molecules to be preferentially packaged inside each chimeric particle. Since dual or triple baculovirus expression vectors are used, which contain a cDNA with a ligand engineered into the coat protein gene and another hybrid cDNA that contains a therapeutic gene grafted to the packing signal, any chimeric particle resulting from the baculovirus expression contains a ligand on the surface and the therapeutic gene of interest inside. The packing signal is placed downstream of the 3' end of the gene sequence since it only acts to tether the gene to the inside of the particle through RNA-protein interactions between the packaging signal and specific coat protein residues exposed on the interior of the particle.

The embodiments of the gene delivery embodiments relate to the ability to create a viral-like particle with ligands on the surface and the mRNA of a gene of therapeutic interest inside that has been preferentially encapsidated based on its association with the encapsidation signal.

Such a system is characterized by a particle consisting of a ligand on the surface and containing a copy of the RNA 2 mRNA as well as a polynucleotide comprising the RNA 2 encapsidation signal contiguous with the selected heterologous gene.

The normal packing constraint on a such particle limits the enclosed polynucleotide to a size of approximately 4,500 bases. The wild-type particle usually contains one copy of the wild-type RNA 2 coat protein mRNA, which is 1,400 bases, and one copy of the RNA 1 polymerase mRNA, which is approximately 3,100 bases. Since the RNA 1 can be omitted in cell culture systems, the particle can preferentially package anything with a intact encapsidation signal from RNA 2. If a chimeric RNA 2 coat protein gene that contains the normal sequence through the encapsidation signal region as well as the inserted sequence for the ligand is co-transfected into insect cells along with a second construct consisting of the RNA 2 encapsidation signal only grafted to a gene of therapeutic interest, the resulting particle will contain one copy each of the chimeric RNA 2 mRNA (about 1,400 bases) and the RNA 2 encapsidation signal-:therapeutic gene. Thus, the maximum size of the therapeutic gene can be approximately 3,100 bases since the packing signal is only approximately 30 bases.

Alternatively, since the RNA 2 coat protein mRNA does not need to be packaged since replication is not necessary, if conservative base changes are introduced into the encapsidation region of the RNA 2 cDNA containing the ligand, the particle will assemble, but only package the RNA 2 encapsidation signal:therapeutic gene mRNA and not the RNA 2 chimeric coat protein mRNA since the stem loop structure has been disrupted in the case of the latter. In this manner, one can essentially fill each particle with approximately 4,500 bases (4.5 kB) of messenger-sense RNA representing therapeutic gene products. These are immediately available for translation by cellular ribosomes upon internalization and uncoating of the particle. Previous work has shown that the 5' end of the transcript is released first to allow for rapid translation by ribosomes.

The ability to encapsidate genes of therapeutic interest also applies to encapsidating mRNA coding for B or T cell epitopes. In particular, the ability to translate mRNA coding for T-cell epitopes introduces the T-cell peptides into the cell where they can be processed by the classic endogenous pathway and presented in a Class I-restricted manner.

The gene delivery system can also be used to accommodate antisense technology since one can create a RNA 2 encapsidation signal:antisense strand easily and package up to 4,500 bases of antisense strands inside each particle that can work according to antisense principles once released into the cytosol. Ribozyme technology may also be used to incorporate ribozyme catalytic centers into antisense RNAs, creating the ability to site-specifically cleave target RNA substrates (Rossi, J. J. 1995. *TIBTECH* 13:301–306).

EXAMPLE 1

Chimeric nodavirus capsid proteins were produced comprising the Vesicular Stomatitis virus (VSV) G glycoprotein B cell epitope TyrThrAspIleGluMetAsnArgLeuGlyLys (Table 3, above, SEQ ID NO:1). Previous work has demonstrated that antibodies against this epitope interfere with transport of VSV-G (Kreis, T. E. 1986. *EMBO J.* 5:931–941). This epitope was engineered into the FHV coat protein gene and chimeric particles were subsequently used to demonstrate an antigenic response in vivo.

The molecular construction of these chimeric coat protein genes was achieved by single-stranded plasmid DNA oligonucleotide-mediated mutagenesis (Kunkel, T. A. 1985. *Rapid and efficient site-specific mutagenesis without phenotypic selection. PNAS* 82:488–492, Kunkel, T. A., Roberts, J. D., and Zakour, R. A. 1987. *Rapid and efficient site-specific mutagenesis without phenotypic selection. Meth. Enzymol.* 154:367–382.). This scheme involves a DNA sequence that can be specifically altered by synthesizing the desired sequence change within an oligonucleotide, and then converting this into a biologically active circular DNA strand by using the oligonucleotide to prime in vitro synthesis on a single-stranded circular DNA template.

A uridine containing ssDNA template is produced by growing M13 phage in the presence of uridine. A mutagenic primer is then annealed to the template DNA followed by extension of the primer with T7 DNA polymerase and ligation to circularize the product. A DNA duplex is thereby created in which one strand is the original template and contains uridine, while the second strand is mutant and does not contain uridine. Transfection of this DNA into DH5αF' cells leads to preferential duplication of the non-uridine containing mutant strands. When transformed cells are plated onto a lawn of untransformed cells, about 70% of the plaques that develop contain the mutagenized sequences.

The bacterial strain used for transformation and phage growth was *E. coli* DH5αF' [F' f80dlacZDM15 D(lacZYA-argF)U169 deoR recA1 hsdR17 ($r_k^-$,$m_k^{30}$) supE44 $1^-$ thi-1 gyrA96 relA1] from Life Technologies (Gaithersburg, Md.). *E. coli* B313/P3 [Hfr PO45 lysA dut ung thi-1 recA spoT1 {P3: $Kan^R$ $Amp^R$ (am) $Tet^R$ (am)] from Invitrogen Corporation (San Diego, Calif.) were used for the growth of uridine containing M13 template DNA. Mutagenesis was performed on sequences cloned into M13mp18 phage DNA obtained from Life Technologies (Gaithersburg, Md.).

The plasmid p2BS(+)-wt served as the starting material for site-directed mutagenesis experiments. This plasmid was a modified pBluescript(+) (Strategene; San Diego, Calif.) into which a 1,400 base pair sequence containing the entire coding region of the RNA 2 gene has been cloned. The RNA 2 coding sequence was cloned into M13mp18 by first subcloning a portion of it into pBluescript-KS(+). The RNA 2 sequence contains a unique AccI site at nucleotide 124 and a XbaI site at its 3' end (nucleotide 1,400), which had been previously engineered in. This 1,276 bp fragment was cloned into the AccI and XbaI sites of pBluescript-KS(+), resulting in a plasmid with a KpnI site adjacent to the AccI site at the 5' end of the inserted sequence. The sequence was then excised with KpnI and XbaI and subcloned into the corresponding sites in M13mp18 replicative form (RF) DNA. In the resultant M13mp18:RNA2-AccI/XbaI clones, the (+) strand of the phage DNA contains the message strand (mRNA) sequence of the RNA 2 gene.

A M13mp18:RNA2-AccI/XbaI phage stock was produced by picking one phage plaque into 1 ml of LB broth. To prepare uridine containing M13mp18:RNA2-AccI/XbaI ssDNA, a 5 ml culture of BW313/P3 cells in midlog phase growth was added to 100 ml of LB broth along with 100 μl of M13mp18:RNA2-AccI/XbaI phage stock. The culture was incubated overnight at 37 degrees Celsius with vigorous shaking. Bacterial cells were pelleted by centrifugation at 5,000×g, and the phage were precipitated from the supernatant by adding ¼ volume of 15% polyethylene glycol (PEG 8000), 2.5 M NaCl, chilling on ice for one hour, and centrifugation at 5000×g for 15 minutes. The precipitated phage were resuspended in 5 ml of 10 mM Tris HCl, 1 mM EDTA, pH 8.0, placed on ice for one hour and then recentrifuged at 5,000×g for 30 minutes to remove debris. The supernatant was extracted twice with equal volumes of phenol/chloroform, ethanol precipitated and resuspended in water at 100 μg/ml.

Mutagenic oligonucleotide primers were designed for the insertion of the different peptide coding sequences between bases encoding amino acids 207 and 208 of the RNA 2 primary amino acid sequence of the capsid protein. Mutagenic primers contained 15 bases that were complementary to the RNA2 message strand sequence on either side on the insertion site, with an intervening central sequence that encoded the peptide to be expressed. To date, the peptide encoding sequence has been up to 78 base pairs, yielding mutagenic oligonucleotide primers with a total length of up to 108 base pairs, and peptide insertions of up to 26 amino acids. The sequence composition of the primers was:

5' CGAACTGGTGGCTGG . . . $(N)_{78}$ . . . ATCTGTTGCAACCGG 3' (Nucleic acid residues 1–15 and 49–63 of SEQ ID NO 20)

where the 15 bases at the 5' and 3' ends of the oligonucleotide are complementary to bases 629–643 and 644–658 of the RNA2 message strand sequence in p2BS(+)-wt, and $(n)_{78}$ is the number of nucleotides encoding the peptide sequence to be expressed.

A molar ratio of mutagenic oligonucleotide to ssDNA template of 10:1 was used in all experiments. Typical reactions used 1 μg of M13mp18:RNA2-AccI/XbaI ssDNA and therefore required 100–200 ng of primer, dependent upon primer length. An amount of primer appropriate for one reaction was phosphorylated by incubation with 10 U T4 polynucleotide kinase in 70 mM Tris-HCl, 10 mM $MgCl_2$, 5 mM DTT, 2 mM ATP, pH 7.6, for 60 minutes at 37 degrees Celsius in a volume of 20 μl. Kinase reactions were terminated by the addition of EDTA to 15 mM, followed by incubation at 70 degrees Celsius for 3 minutes.

To anneal the phosphorylated primers to the template DNA, 1.25 μl of 10×SSC (10×SSC is 1.5 M NaCl, 0.15 M $Na_3CitrateH_2O$, pH 7.0) was added to the kinase reaction mixture along with 1 μg of M13mp18:RNA2-AccI/XbaI ssDNA and the volume was adjusted to 40 μl. The mixture was submerged in a 500 ml water bath at 95 degrees Celsius and the primers were annealed by allowing the bath to cool slowly to room temperature.

The annealed mutagenic primers were extended with T7 DNA polymerase and circularized with T4 DNA ligase. Synthesis and ligation were performed simultaneously in a 100 μl volume containing the entire primer-template annealing mixture, 20 mM Tris HCl (pH 8.0), 10 mM $MgCl_2$, 2 mM dithiothreitol, 2 mM ATP, 1 mM dATP, dGTP. dCTP, and dTTP, 0.1 mg bovine serum albumin, 10 U T7 DNA polymerase and 3 U T4 DNA ligase. Incubation was for 2 hours at 37 degrees Celsius and the reaction was terminated by the addition of EDTA to 15 mM.

A 20 μl aliquot of each reaction was analyzed by gel electrophoresis in a 1.0% agarose gel. Successful reactions resulted in the conversion of essentially all ssDNA template DNA to high molecular weight double-stranded replicative form DNA.

The remaining product from the primer extension reaction was ethanol precipitated, dried, and resuspended in 10 μl of water. Competent DH5αF' cells were transformed with 1 μl of the resuspended reaction product mixture according to the manufacturers protocol. The transformed cells were plated on a lawn of DH5αF' cells according to the manufacturers recommendations and plates were incubated at 37 degrees Celsius. Phage plaques became visible within 12 hours.

Mutagenized clones were identified and confirmed by DNA sequence analysis. Single phage plaques were isolated and ssDNA was prepared as described above. The DNA was sequenced using T7 Sequenase v2.0 (Amersham Life Science; Cleveland, Ohio) according to the manufacturers protocol. The biological selection against uridine containing template DNA is very strong, and the efficiency of mutant recovery was typically over 70%.

Mutagenized sequences from selected clones were recovered for subcloning from double-stranded replicative form (RF) DNA. Phage infected DH5αF' cells were grown as described above for the isolation of ssDNA, and the cell pellet was processed for RF isolation according to standard protocols for the isolation and banding of plasmids by cesium chloride-ethidium bromide density gradient centrifugation.

The RF DNA was digested with AccI and XbaI and the resulting RNA2 fragment, now carrying an inserted sequence, was subcloned back into the original AccI/XbaI sites in p2BS(+)-wt. All molecular constructs were subjected to complete DNA sequencing and analysis prior to expression.

The FHV chimera coat protein genes were then expressed in the highly efficient baculovirus expression system using standard expression and confirmation procedures (Vlak, J .M. and Keus, R. J. A. 1990. *In Viral Vaccines*. Wiley-Liss, Inc., New York. pp. 91–128.; O'Reilly, D. R., Miller, L. K., and Luckow, V. A. 1992. *Baculovirus Expression Vectors: A Laboratory Manual.* W. H. Freemnan and Co., New York). The baculovirus expression system has been found to be a particularly efficient system at generating recombinant proteins. Recombinant proteins are usually produced at levels ranging between 0.1% and 50% of the total insect protein. In addition, the baculovirus expression system within insect cells is typically capable of performing most of the processing events that are required for forming biologically active foreign proteins.

cDNAs of FHV RNA 2 encoding either wild-type or chimeric coat protein alpha was placed under control of the baculovirus polyhedron promoter and inserted into the baculovirus genome by homologous recombination. The mRNAs of the coat protein expressed in the heterologous system are longer than the 1,400 bases comprising authentic FHV RNA 2. This is because the sequence of RNA 2 lacks eukaryotic transcription termination and polyadenylation signals, which are provided by the flanking polyhedron sequences. The final wild-type transcripts are about 2,100 bases long, including a poly(A) tail, which is not present in authentic FHV RNA 2. This system produces high yields of particles in the absence of RNA 1 and in the presence of a significantly larger RNA 2 (Schneemann, A. et al. 1993. *J. Virol.* 67:2756–2763).

Recombinant baculoviruses containing the chimeric FHV coat protein cDNAs were generated by cotransfection of the RNA 2 cDNA with wild-type linearized *Autographa californica* mononuclear polyhedrosis virus (AcMNPV) into a monolayer of $2\times10^6$ *S. frugiperda* cells. The cells were covered with 1 ml of TMN-FH medium (Pharmingen, San Diego, Calif.). The RNA 2 cDNA and baculoviral DNA were mixed in 30 $\mu$g of lipofectin and brought up to a total volume of 100 $\mu$l. This transfection mixture was added to the 1 ml of medium covering the cells in a dropwise manner. After 4 hours incubation at 27 degrees Celsius, the medium was removed and replaced with fresh TMN-FH medium. Single recombinant viruses were isolated by several rounds of plaque purification. The isolated recombinants were amplified to a titer exceeding $10^8$ pfu/ml.

The FHV chimeric particles containing the epitopes of interest were purified from recombinant baculovirus-infected cells 4–7 days after infection. Cells were lysed in the presence of 0.5% NP-40 and 0.1% 2-mercaptoethanol (2-ME). After incubation on ice for 15 minutes, the cell debris was pelleted at 10,000 rpm in a Beckman GS-15R centrifuge. The supernatant was treated with RNase A at a final concentration of 10 $\mu$g/ml for 30 minutes at 27 degrees Celsius, followed by centrifugation at 10,000 g to remove any particulate matter. The resulting supernatant, which contained the particles, was layered onto a 30% (w/w) sucrose cushion containing 50 mM Hepes (N-2-hydroxyethylpiperazine-N-2-ethanesulfonic acid) (pH 7.0), 0.1% 2-ME, and 0.1% bovine serum albumin. The particles were pelleted through the sucrose cushion in a Beckman JS 24.15 rotor at 100,000 g for 2.5 hours at 7 degrees Celsius. The supernatant was removed and the pellet containing the virus particles was resuspended in 50 mM Hepes and 0.1% 2-ME. The suspension was layered on a 15 ml 10 to 40% (w/w) linear sucrose gradient and sedimented in a JS 24.15 rotor at 100,000 g for 1.5 hours at 7 degrees Celsius. For analytical yields, the gradient was fractionated on an ISCO gradient fractionator at 0.75 ml per minute and 0.5 minute per fraction. Fractions containing virus particles as measured by optical density were stored at 4 degrees Celsius or frozen at −20 degrees Celsius. For larger yields, fractionation was not necessary. Instead, after centrifugation, a viral band could be observed in the upper ⅓ of the gradient. An 18-gauge needle connected to a syringe was then used to puncture the tube and withdraw the virus fraction.

For very large yields in SF9 or T. ni. cells, the FHV chimeric particles containing the epitopes of interest were purified from recombinant baculovirus-infected cells 7 days after infection. Cells were lysed in the presence of 0.5% NP-40 and 0.1% 2-ME. After incubation on ice for 15 minutes, the cell debris was pelleted at 10,000 rpm in a Beckman GS-15R centrifuge. Polyethylene glycol 8,000 (PEG 8,000) was added to the resulting supernatant at a final concentration of 8% and NaCl to a final concentration of 0.2 M. The suspension was mixed on ice for 1 hour during which time the PEG 8,000 dissolved.

The turbid suspension was centrifuged at 14,000 g for 10 minutes, and the pellet was resuspended in 20 ml of Hepes buffer (pH 7.0). Insoluble material was removed by centrifugation at 14,000 g for 20 minutes. The supernatant was withdrawn and saved. The PEG pellet was resuspended 2 more times with aliquots of 20 ml of Hepes buffer followed by centrifugation. The supernatants were pooled and layered onto 10 to 40% (w/w) linear sucrose gradients and purified as discussed above.

An optional additional purification step can be used where the isolated particles from the sucrose gradient are diluted fourfold with 50 mM Hepes (pH 7.0 and 0.1% 2-ME and pelleted through a 15 ml 20 to 45% (w/w) CsCl gradient in Hepes (pH 7.0) and 0.1% 2-ME in a JS 24.15 or comparable rotor at 100,000 g for 16 hours at 7 degrees Celsius.

The isolated particles were dialyzed extensively in Hepes buffer (pH 7.0) to remove the sucrose or CsCl. Batches for testing in animals were filter-sterilized and stored at −20 degrees Celsius.

The analysis of the Nodavirus chimeric particles has been completed by two primary methods. One method utilizes a Western blot that uses immunochemical reagents to detect specific proteins of interest. 180 copies of the newly synthesized coat protein molecules are assembled within minutes into labile precursor particles, called provirions. The assembly process triggers an spontaneous chemical reaction that cleaves the immature coat protein into two smaller ones, both of which remain part of the mature virion (virus particle). The presence of a 43 kDa band (uncleaved), a 38 kDa band (beta) and a 5 kDA band (gamma) indicate the particles have assembled. After a few days, most of the uncleaved product is gone and only major bands of 38 kDa and 5 kDa are detectable at that point. A substantial body of previous work has shown that this cleavage process only occurs in particles that have assembled (Gallagher, T. M. and R. R. Rueckert. 1988. *J. Virol.* 62:3399–3406; Schneemann, A. et al. 1992. *J. Virol.* 66:6728–6734).

The FHV:VSV chimeras produced in the baculovirus system were analyzed by Western analysis. Proteins from Sf cells infected with recombinant baculovirus containing RNA2:VSV were isolated and separated by standard SDS-polyacrylamide gel electrophoresis and analyzed on immunoblots with antibodies directed against the capsid protein and the desired peptides. The antibodies directed against normal FHV sequences detect these bands, and antibodies directed against the inserted sequences detect the respective inserted epitopes within the context of the coat protein. These immunochemical experiments demonstrate that the cleavage products are all present, which are slightly larger than normal due to the inserted sequence, and confirms that the chimeric particles have assembled.

In another manner of confirmation, the chimeric virus-like particles were examined using transmission electron microscopy in order to determine their general geometry and size (Harris, J. R. 1991. *Electron microscopy in biology. A practical approach. The practical approach series.* Oxford University Press, New York).

For negative staining analysis, a drop of the chimeric virus-like particle suspension was applied onto a glow-discharged, Formvar-carbon-coated, 300–400 mesh copper grid. In 1–2 minutes the excess of the liquid was partially blotted, followed by 3×washes in drops of the buffer. The grid was then applied twice and incubated for 1 minutes in a third drop of 1% uranyl acetate (Ted Pella Inc.) aqueous solution filtered through a 0.2 mm Millipore filter. The excess liquid was partially blotted and the grid was air dried. The micrographs were taken on a Phillips CM100 electron microscope at 100 kV.

For immunoelectron microscopy, viral chimeric particles were incubated with the primary antibody. 0.2 mg of chimeric virus in 50 mM HEPES, pH 7.0 (0.4 mg/ml virus) was incubated with 0.012 mg Anti-VSV-G MAb (dissolved in the same buffer) overnight at 4 degrees Celsius with gentle shaking. For immuno-gold-labeling, a drop of the antibody-virus mixture (10 ml) was laid on a Formvar-carbon-coated, 300–400 mesh copper grid for approximately 1 min. The excess was partially blotted, and the grids were washed 5×in 50 mM HEPES, pH 7.0 to remove the unbound antibody. Then the grids were incubated in drops of 6 nm Colloidal Au-Donkey Anti-Mouse IgG (1:10 dilution with the buffer) for 30 minutes, at room temperature and constant humidity, followed by 5×washes in buffer. Afterwards, the specimens were incubated for 1 minute with 1% uranyl acetate, completely blotted, and air-dried.

EXAMPLE 2

Chimeric capsid proteins were produced that included the epitope from the Bovine Respiratory Syncytial virus (BRSV) F protein as shown in Table 3. Specifically, a BRSV F protein sequence AspLysGluLeuLeuProLysValAsnAsnHis AspCysGlnIleSerAsnIleAlaThrValIleGluPheGlnGln (SEQ ID NO:2) was engineered into the FHV coat protein gene as described in detail in Example 1, above.

The BRSV F glycoprotein is known to be an important antigen in the immune response following infection. This sequence has been shown to be a B cell epitope and also contains sequences necessary for a proliferative T-cell response (Corvaisier, C., et al. 1993. *Res. Virol.* 144:141–150). Following expression and subsequent purification, the particles were used as a vaccine in vivo to demonstrate their antigenicity.

The FHV:BRSV chimeras produced in the baculovirus system were analyzed by Western analysis. Proteins from Sf cells infected with recombinant baculovirus containing RNA2:BRSV were isolated and separated by standard SDS-polyacrylamide gel electrophoresis and analyzed on immunoblots with antibodies directed against the capsid protein and the desired peptides. The antibodies directed against normal FHV sequences detect these bands, and antibodies directed against the inserted sequences detect the respective inserted epitopes within the context of the coat protein. These immunochemical experiments demonstrate that the cleavage products are all present, which are slightly larger than normal due to the inserted sequence, and confirms that the chimeric particles have assembled.

EXAMPLE 3

Clearance of HBV depends on a vigorous and polyclonal B cell and T cell response to the envelope, nucleocapsid, and polymerase antigens of the virus. The CTL response to HBV is not easily detected in chronically infected patients who have been unable to clear virus. While it has been assumed that viral clearance requires the destruction of infected hepatocytes, which can cause the associated liver disease, new evidence suggests that this may not be the case. Recent studies indicate that HBV-specific CTLs can clear the virus from the livers of transgenic mice that have high levels of HBV replication that are comparable to levels found in infected human liver. These studies enabled the intracellular inactivation of HBV by infecting mice with lymphocytic choriomeningitis virus (LCMV), which caused a secondary infection. This clearance occurs without injuring the once-infected hepatocytes, which revert to a healthy HBV-negative status. This curative effect is mediated by interferon gamma (IFN-γ) and tumor necrosis factor alpha (TNF-α) that CTL secrete upon activation.

The cytokines activate the hepatocytes to perform at least two curative antiviral functions that eliminate all traces of replicating virus intracellularly. First they disassemble the HBV nucleocapsid particles present in the cytoplasm, exposing the viral genome to cellular nucleases. Second, they degrade viral DNA, thereby precluding the production of new transcriptional template and the assembly of new viral particles. These events occur in perfectly viable hepatocytes that are cytologically entirely normal.

The studies discussed above demonstrate that CTL can cure chronic Hepatitis B virus infection without killing the infected cells. This demonstrates that viral clearance is mainly a survival function of the infected cells rather than a destructive function of the immune response.

In this example, an FHV chimeric particle that carries a hepatocyte-specific ligand and containing human interferon-γ packaged by use of the encapsidation signal (FIGS. 2 and 12) has been effectively targeted to liver cells so it can act as a gene delivery system.

This liver-specific ligand is based on the sequence of the *Plasmodium falciparum* CSP: VIII (SEQ ID NO:8), that effectively blocks the binding of *Plasmodium falciparum* circumsporozoite protein to hepatocyte membranes (Cerami et al. 1992. *Cell, Vol.* 70, 1021–1033). Oligonucleotide-mediated mutagenesis was used to insert a slightly larger CSP coding sequence, IX (23 amino acids, SEQ ID NO:9) between FHV RNA 2 amino acid residues 207 and 208 (FIG. 12), in an attempt to generate an RNA2:CSP fusion protein that specifically binds hepatocyte membranes. Once these assembled chimeric particles are introduced to liver cells, the liver cell-specific molecules, or ligands, on the particle surface bind directly to other molecules in the liver cell. Since the same particle has the message for IFN-γ inside, its entry into liver cells causes localized production of interferon. This localized interferon-_γ in liver cells acts in a autocrine and paracrine mode to activate the in vivo production of more of this cytokine within those cells, which can clear the virus without killing the cells.

EXAMPLE 4

The present system can be readily applied to other peptide ligands less than about 100 amino acid residues in length, and many genes less than approximately 4,500 bases in size. Cytokines and T cell epitopes represent a small number of these candidate genes or gene fragments. A motor neuron targeting system that has a variety of medical uses can be constructed as well. In a similar manner as previously discussed, a ligand is expressed that binds specifically to motor neuron nerve terminals on the surface of the particle and facilitates the gene delivery system. There are several activity dependent nerve terminal strains whose activity is based upon the fact that after neurotransmitter vesicle fusion, the vesicles are rapidly taken back up and pick up some of the fluid from the synaptic cleft in the process (Mundigl O. 1995. *Eur J Cell Biol* 66: 246–256). A target for virus binding that is inside the synaptic vesicle is efficient. The particle is about 300 Å in diameter and fits into endocytotic vesicles.

A synaptic vesicle targeting approach involves the Fc antibody binding region of protein A, which can be expressed on the surface of the particle, and then targeting it to any antigen necessary simply by binding the particle to specific antibodies prior to administering it to the animal. By using structure-based design and phage display methods, 33 residues of protein A have been found to bind the Fc region (Braisted A. C and Wells J. A. 1996. *Proc Natl Acad Sci USA* 93:5688–569). This obviates the need to identify receptors and make a new chimeric virus each time. The same core chimeric particle with the Fc antibody region of protein A can be used in many applications by conjugating it to different antibodies.

EXAMPLE 5

Small molecules such as peptides, or haptens, while able to interact with immune response components, are not fully immunogenic. These small molecules can be made immunogenic by coupling them to carrier proteins that are capable of presenting the haptens in an immunogenic manner. Some commonly used carriers that covalently couple to haptens include keyhole limpet hemocyanin (KLH) with a molecular weight of $4.5 \times 10^5$ to $1.3 \times 10^7$ Dalton, bovine serum albumin (BSA) with a molecular weight of 67,000 Dalton and ovalbumin (OVA) with a molecular weight of 45,000 Dalton.

The Nodaviruses, and specifically the FHV particle with a molecular mass of approximately $7.7 \times 10^6$ Dalton, are capable of functioning as highly efficient carriers of antigenic peptides on their surface, which peptides have been covalently attached through conjugation chemistry. As the particle dissociates into individual subunits, the antigenic peptides become increasingly exposed and immunogenic.

The conjugation chemistry used in this system stems from the fact that there are about 10 amine side chains and 7 acid side chains per subunit that are exposed. This implies that there about 1,800 amine side chains and 1,260 acid side chains per particle. These numbers apply to the wild-type particle, which itself is capable of conjugating numerous peptides to each particle. Chimeric particles with additional amine side chains and acid side chains engineered into the insertion loop serve to increase the number of sites available for conjugation. There are no exposed sulfhydryl groups present on the wild-type particle, which presents the ability to construct an efficient conjugation scheme. Most of the residues in the insertion loop would be accessible on the surface of the particle.

In this particular example, sulfonated crosslinkers were used to conjugate peptides to the surface of the particles. Specifically, the crosslinker sulfosuccinimid 4-(N maleimidomethyl) cyclohexane-1-carboxylate was used in this example. This crosslinker has an NHS-ester and a maleimide group connected with a spacer arm. NHS-esters react with primary amines and maleimides react with sulfhydryls. The NHS reaction is performed first by incubating a 50 molar excess of crosslinker to FHV particles and allowing the reaction to proceed for 30 minutes at room temperature. A second aliquot of crosslinker was added to bring the crosslinker to a final 100 molar excess and allowing the reaction to proceed for 30 additional minutes at room temperature. Excess crosslinker was removed by quenching the NHS-ester reaction by the addition of Tris-HCl pH 7.0 to a final concentration of 0.1 M, followed by addition of peptides with the sulfhydryl groups. The crosslinking is effective since NHS esters react with primary amines at pH 7–9 and maleimides react with SH groups at pH 6.5–7.5.The free amines in the Tris-HCL react with the remaining available NHS-esters. Moreover, since maleimides only react with NHS-esters at a high pH, the reactivity of these two groups with each other does not present a problem.

A portion of the BRSV peptide used previously (SEQ ID NO:22) and having amino acid residues CysAspLysGluLeuLeuProLysValAsnAsnHisAspCys GlnIleSer (SEQ ID NO:45) was used as a hapten. A Cys residue at the amino terminus of this portion was added during synthesis to allow for conjugation with KLH. In a separate conjugation, the same BRSV peptide portion but without the additional Cys at the amino terminus, i.e., AspLysGluLeuLeuProLysValAsn AsnHisAspCysGlnIleSer (SEQ ID NO:46), was used. These peptides were conjugated to wild-type particles as well as FHV:VSV chimeras using the scheme outline above. The particles were then denatured and analyzed by Western Blot, and the presence of multiple peptides within the context of a coat protein monomer was confirmed. The conjugated particles were subsequently used as immunogens and found to induce a strong immune response against the BRSV peptides that had been conjugated to the particles.

This demonstrates that the particle, even in the absence of an insertion in the capsid protein gene, can serve as an effective immunostimulant and immunomodulator. Furthermore, the immunostimulatory and immunomodulatory effects are enhanced by the presence of inserted sequences in the capsid protein gene as well as by encapsidating other known immunostimulants such as cytokines inside the particle prior to conjugating haptens to the surface.

EXAMPLE 6

Other therapeutic constructs are possible such as antimalarial targeting. For antimalarial therapy, one designs a gene therapy protocol using the present system that targets malarial sporozoite cells instead of human cells. Expression of the CSP-recognition receptor site on the FHV virus coat protein binds up and blocks the parasite while it is still in the bloodstream and thereby prevents infection, or delivers a toxigenic to the parasite, thereby destroying it.

The preceding written description provides a full, clear, concise and exact disclosure of the invention so as to enable one skilled in the art to make and use the same. This disclosure should not be construed so as to impart any direct or implied limitation upon the scope of the invention which is particularly pointed out and distinctly claimed below.

SEQUENCE LISTING (1) GENERAL INFORMATION:

(iii) NUMBER OF SEQUENCES: 46

(2) INFORMATION FOR SEQ ID NO: 1:

(i) SEQUENCE CHARACTERISTICS:
          (A) LENGTH:  11 amino acids
          (B) TYPE:   amino acid
          (C) STRANDEDNESS: Not Relevant
          (D) TOPOLOGY:  unknown (ii) MOLECULE TYPE:  peptide (xi) SEQUENCE DESCRIPTION:   SEQ ID NO: 1:

Tyr Thr Asp Ile Glu Met Asn Arg Leu Gly Lys
1               5                   10

(2) INFORMATION FOR SEQ ID NO: 2:

(i) SEQUENCE CHARACTERISTICS:
          (A) LENGTH:   26 amino acids
          (B) TYPE: amino acid
          (C) STRANDEDNESS: Not Relevant
          (D) TOPOLOGY:  unknown (ii) MOLECULE TYPE:  peptide (xi) SEQUENCE DESCRIPTION:   SEQ ID NO: 2:

Asp Lys Glu Leu Leu Pro Lys Val Asn Asn His Asp Cys Gln Ile Ser
1               5                   10                  15

Asn Ile Ala Thr Val Ile Glu Phe Gln Gln
20                  25

(2) INFORMATION FOR SEQ ID NO: 3:

(i) SEQUENCE CHARACTERISTICS:
        (A) LENGTH:  26 amino acids
        (B) TYPE:  amino acid
        (C) STRANDEDNESS: Not Relevant
        (D) TOPOLOGY:  unknown (ii) MOLECULE TYPE:  peptide (xi) SEQUENCE DESCRIPTION:  SEQ ID NO: 3:

```
Asp Lys Gln Leu Leu Pro Ile Val Asn Lys Gln Ser Cys Ser Ile Ser
1               5                   10                  15
Asn Ile Glu Thr Val Ile Glu Phe Gln Gln
20                  25
```

(2) INFORMATION FOR SEQ ID NO: 4:

(i) SEQUENCE CHARACTERISTICS:
        (A) LENGTH:  26 amino acids
        (B) TYPE:  amino acid
        (C) STRANDEDNESS: Not Relevant
        (D) TOPOLOGY:  unknown (ii) MOLECULE TYPE:  peptide (xi) SEQUENCE DESCRIPTION:  SEQ ID NO: 4:

```
Asp Lys Arg Leu Leu Pro Ile Val Asn Gln Gln Ser Cys Arg Ile Ser
1               5                   10                  15
Asn Ile Glu Thr Val Ile Glu Phe Gln Gln
20                  25
```

(2) INFORMATION FOR SEQ ID NO: 5:

(i) SEQUENCE CHARACTERISTICS:
        (A) LENGTH:  6 amino acids
        (B) TYPE:  amino acid
        (C) STRANDEDNESS: Not Relevant
        (D) TOPOLOGY:  unknown (ii) MOLECULE TYPE:  peptide (xi) SEQUENCE DESCRIPTION:  SEQ ID NO: 5:

```
Phe Pro Ser Asp Glu Phe
1               5
```

(2) INFORMATION FOR SEQ ID NO: 6:

(i) SEQUENCE CHARACTERISTICS:
        (A) LENGTH:  14 amino acids
        (B) TYPE:  amino acid
        (C) STRANDEDNESS: Not Relevant
        (D) TOPOLOGY:  unknown (ii) MOLECULE TYPE:  peptide (xi) SEQUENCE DESCRIPTION:  SEQ ID NO: 6:

```
Gln Asp Pro Arg Val Arg Gly Leu Tyr Phe Pro Ala Gly Gly
1               5                   10
```

(2) INFORMATION FOR SEQ ID NO: 7:

(i) SEQUENCE CHARACTERISTICS:
        (A) LENGTH:  27 amino acids
        (B) TYPE:  amino acid
        (C) STRANDEDNESS: Not Relevant
        (D) TOPOLOGY:  unknown (ii) MOLECULE TYPE: peptide (xi) SEQUENCE DESCRIPTION: SEQ ID NO: 7:

Leu Gln Ala Gly Phe Phe Leu Leu Thr Arg Ile Leu Thr Ile Pro Gln
1               5                   10                  15

Ser Leu Asp Ser Trp Trp Thr Ser Leu Asn Phe
20                  25

(2) INFORMATION FOR SEQ ID NO: 8:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: unknown (ii) MOLECULE TYPE: peptide (xi) SEQUENCE DESCRIPTION: SEQ ID NO: 8:

Pro Cys Ser Val Thr Cys Gly Asn Gly Ile Gln Val Arg Ile Lys Pro
1               5                   10                  15

Gly Ser Ala Asn
20

(2) INFORMATION FOR SEQ ID NO: 9:

(i) SEQUENCE CHARACTERISTICS:
            (A) LENGTH: 23 amino acids
            (B) TYPE: amino acid
            (C) STRANDEDNESS: Not Relevant
            (D) TOPOLOGY: unknown (ii) MOLECULE TYPE: peptide (xi) SEQUENCE DESCRIPTION: SEQ ID NO: 9:

Glu Trp Ser Pro Cys Ser Val Thr Cys Gly Asn Gly Ile Gln Val Arg
1               5                   10                  15

Ile Lys Pro Gly Ser Ala Asn
20

(2) INFORMATION FOR SEQ ID NO: 10:

(i) SEQUENCE CHARACTERISTICS:
            (A) LENGTH: 407 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 10:

Met Val Asn Asn Asn Arg Pro Arg Arg Glu Arg Ala Glu Arg Val Val
1               5                   10                  15

Val Thr Thr Thr Glu Thr Ala Pro Val Pro Glu Glu Asn Val Pro Arg
20                  25                  30

Asn Gly Arg Arg Arg Arg Asn Arg Thr Arg Arg Asn Arg Arg Arg Val
35                  40                  45

Arg Gly Met Asn Met Ala Ala Leu Thr Arg Leu Ser Gln Pro Gly Leu
50                  55                  60

Ala Phe Leu Lys Cys Ala Phe Ala Pro Pro Asp Phe Asn Thr Asp Pro
65                  70                  75                  80

Gly Lys Gly Ile Pro Asp Arg Phe Glu Gly Lys Val Val Ser Arg Lys
85                  90                  95

```
Asp Val Leu Asn Gln Ser Ile Ser Phe Thr Ala Gly Gln Asp Thr Phe
100                 105                 110
Ile Leu Ile Ala Pro Thr Pro Gly Val Ala Tyr Trp Ser Ala Ser Val
115                 120                 125
Pro Arg Gly Thr Phe Pro Thr Ser Ala Thr Thr Phe Asn Pro Val Asn
130                 135                 140
Tyr Pro Gly Phe Thr Ser Met Phe Gly Thr Thr Ser Thr Ser Arg Ser
145                 150                 155                 160
Asp Gln Val Ser Ser Phe Arg Tyr Ala Ser Met Asn Val Gly Ile Tyr
165                 170                 175
Pro Thr Ser Asn Leu Met Gln Phe Ala Gly Ser Ile Thr Val Trp Lys
180                 185                 190
Cys Pro Val Lys Leu Ser Thr Val Gln Phe Pro Val Ala Thr Asp Pro
195                 200                 205
Ala Thr Ser Ser Leu Val His Thr Leu Val Gly Leu Asp Gly Val Leu
210                 215                 220
Ala Val Gly Pro Asp Asn Phe Ser Glu Ser Phe Ile Lys Gly Val Phe
225                 230                 235                 240
Ser Gln Ser Ala Cys Asn Glu Pro Asp Phe Glu Phe Asn Asp Ile Leu
245                 250                 255
Glu Gly Ile Gln Thr Leu Pro Pro Ala Asn Val Ser Leu Gly Ser Thr
260                 265                 270
Gly Gln Pro Phe Thr Met Asp Ser Gly Ala Glu Ala Thr Ser Gly Val
275                 280                 285
Val Gly Trp Gly Asn Met Asp Thr Ile Val Ile Arg Val Ser Ala Pro
290                 295                 300
Glu Gly Ala Val Asn Ser Ala Ile Leu Lys Ala Trp Ser Cys Ile Glu
305                 310                 315                 320
Tyr Arg Pro Asn Pro Asn Ala Met Leu Tyr Gln Phe Gly His Asp Ser
325                 330                 335
Pro Pro Leu Asp Glu Val Ala Leu Gln Glu Tyr Arg Thr Val Ala Arg
340                 345                 350
Ser Leu Pro Val Ala Val Ile Ala Ala Gln Asn Ala Ser Met Trp Glu
355                 360                 365
Arg Val Lys Ser Ile Ile Lys Ser Ser Leu Ala Ala Ser Asn Ile
370                 375                 380
Pro Gly Pro Ile Gly Val Ala Ala Ser Gly Ile Ser Gly Leu Ser Ala
385                 390                 395                 400
Leu Phe Glu Gly Phe Gly Phe
405
```

(2) INFORMATION FOR SEQ ID NO: 11:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 11:

GGAAGATCTA TGCAGGACCC GTACGTA                                  27

(2) INFORMATION FOR SEQ ID NO: 12:

(i) SEQUENCE CHARACTERISTICS:
        (A) LENGTH: 45 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 12:

```
TAATCTGGTT AGCGCCGCCA TGTTCATTTA CTGGCTAGCG CGACG            45
```

(2) INFORMATION FOR SEQ ID NO: 13:

(i) SEQUENCE CHARACTERISTICS:
        (A) LENGTH: 48 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 13:

```
GGAAGATCTA AACGCCAAAC CAGGTTGACT TAATCTGGTT AGCGCCGC         48
```

(2) INFORMATION FOR SEQ ID NO: 14:

(i) SEQUENCE CHARACTERISTICS:
        (A) LENGTH: 57 base pairs
        (B) TYPE: nucleic acid
        (C) STRANDEDNESS: double
        (D) TOPOLOGY: unknown (ii) MOLECULE TYPE: nucleic acid (xi) SEQUENCE DESCRIPTION: SEQ ID NO: 14:

```
CCAAGCTCGA AATTAACCCT CACTAAAGTA AACAATTCCA AGTTCCAAAA        50
TGGTTAA                                                       57
```

(2) INFORMATION FOR SEQ ID NO: 15:

(i) SEQUENCE CHARACTERISTICS:
        (A) LENGTH: 93 base pairs
        (B) TYPE: nucleic acid
        (C) STRANDEDNESS: double
        (D) TOPOLOGY: unknown (ii) MOLECULE TYPE: nucleic acid (xi) SEQUENCE DESCRIPTION: SEQ ID NO: 15:

```
AAACCAGTTT AAGTCAACAG ACTAAGGTCT AGAGGATCCC CGGGTACCGA        50
GCTCGAATTC GCCCTATAGT GAGTCGTATT ACAATTCACT GGC               93
```

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO: 16:

```
Pro Val Ala Thr Asp Pro Ala Thr Ser Ser
1               5                   10
```

(2) INFORMATION FOR SEQ ID NO: 17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Tyr Thr Asp Ile Glu Met Asn Arg Leu Gly Lys
1               5                   10
```

(2) INFORMATION FOR SEQ ID NO: 18:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Tyr Thr Asp Ile Glu Met Asn Arg Leu Gly Lys
1               5                   10
```

(2) INFORMATION FOR SEQ ID NO: 19:

(i) SEQUENCE CHARACTERISTICS:
        (A) LENGTH: 21 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 19:

```
Pro Val Ala Thr Asp Tyr Thr Asp Ile Glu Met Asn Arg Leu Gly Lys
1               5                   10                  15

Pro Ala Thr Ser Ser
20
```

(2) INFORMATION FOR SEQ ID NO: 20:

(i) SEQUENCE CHARACTERISTICS:
        (A) LENGTH: 63 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 20:

```
CGAACTGGTG GCTGGCTTGC CCAGGCGGTT CATCTCGATG TCCGTGTAAT        50

CTGTTGCAAC CGG                                               63
```

(2) INFORMATION FOR SEQ ID NO: 21:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 21:

CTTGCCCAGG CGGTTCATCT CGATGTCCGT GTA                                     33

(2) INFORMATION FOR SEQ ID NO: 22:

(i) SEQUENCE CHARACTERISTICS:
            (A) LENGTH: 26 amino acids
            (B) TYPE: amino acid
            (C) STRANDEDNESS: Not Relevant
            (D) TOPOLOGY: unknown (ii) MOLECULE TYPE: peptide (xi) SEQUENCE DESCRIPTION: SEQ ID NO: 22:

Asp Lys Glu Leu Leu Pro Lys Val Asn Asn His Asp Cys Gln Ile Ser
1               5                  10                  15

Asn Ile Ala Thr Val Ile Glu Phe Gln Gln
20                  25

(2) INFORMATION FOR SEQ ID NO: 23:

(i) SEQUENCE CHARACTERISTICS:
            (A) LENGTH: 108 base pairs
            (B) TYPE: nucleic acid
            (C) STRANDEDNESS: double
            (D) TOPOLOGY: unknown (ii) MOLECULE TYPE: nucleic acid (xi) SEQUENCE DESCRIPTION: SEQ ID NO: 23:

CCGGTTGCAA CAGATGACAA AGAGCTTCTA CCTAAAGTTA                              40

ACAATCATGA TTGTCAGATA TCCAACATAG CAACTGTGAT                              80

AGAATTCCAA CAACCAGCCA CCAGTTCG                                          108

(2) INFORMATION FOR SEQ ID NO: 24:

(i) SEQUENCE CHARACTERISTICS:
            (A) LENGTH: 108 bases
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO: 24:

CGAACTGGTG GCTGGTTGTT GGAATTCTAT CACAGTTGCT ATGTTGGATA                   50

TCTGACAATC ATGATTGTTA ACTTTAGGTA GAAGCTCTTT GTCATCTGTT                  100

GCAACCGG                                                                108

(2) INFORMATION FOR SEQ ID NO: 25:

(i) SEQUENCE CHARACTERISTICS:
            (A) LENGTH: 33 bases
            (B) TYPE: nucleic acid
            (C) STRANDEDNESS: single
            (D) TOPOLOGY: linear (ii) MOLECULE TYPE: nucleic acid (xi) SEQUENCE DESCRIPTION: SEQ ID NO: 25:

CACAGTTGCT ATGTTGGATA TCTGACAATC ATG                                     33

(2) INFORMATION FOR SEQ ID NO: 26:

(i) SEQUENCE CHARACTERISTICS:
        (A) LENGTH: 95 base pairs
        (B) TYPE: nucleic acid
        (C) STRANDEDNESS: double
        (D) TOPOLOGY: unknown (ii) MOLECULE TYPE: nucleic acid (xi) SEQUENCE DESCRIPTION: SEQ ID NO: 26:

TCGGGCGCGG ATCAGATCTG CAGCGGCCGC GTAAACAATT CCAAGTTCCA                50

AAATGGTTAA GTCAACAGAC TAAGGTCTAG AGGTACCCGG GATCC                    95

(2) INFORMATION FOR SEQ ID NO: 27:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 27:

CAGCGGCCGC GTAAACAATT CCAAGTTCCA AAATGG                               36

(2) INFORMATION FOR SEQ ID NO: 28:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 28:

CCTCTAGACC TTAGTCTGTT GAC                                             23

(2) INFORMATION FOR SEQ ID NO: 29:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO: 29:

Gln Asp Pro Arg Val Arg Gly Leu Tyr Phe Pro Ala Gly Gly
1               5                   10

(2) INFORMATION FOR SEQ ID NO: 30:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO: 30:

Pro Val Ala Thr Asp Gln Asp Pro Arg Val Arg Gly Leu Tyr Phe Pro
1               5                   10                  15

```
Ala Gly Gly Pro Ala Thr Ser Ser
 20

(2) INFORMATION FOR SEQ ID NO: 31:

(i) SEQUENCE CHARACTERISTICS:
        (A) LENGTH: 27 amino acid
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO: 31:

Leu Gln Ala Gly Phe Phe Leu Leu Thr Arg Ile Leu Thr Ile Pro Glu
 1               5                  10                  15

Ser Leu Asp Ser Trp Trp Thr Ser Leu Asn Phe
 20                  25

(2) INFORMATION FOR SEQ ID NO: 32:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 32:

Pro Val Ala Thr Asp Leu Gln Ala Gly Phe Phe Leu Leu Thr Arg Ile
 1               5                  10                  15

Leu Thr Ile Pro Glu Ser Leu Asp Ser Trp Trp Thr Ser Leu Asn Phe
 20                  25                  30

Pro Ala Thr Ser Ser
 35

(2) INFORMATION FOR SEQ ID NO: 33:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO: 33:

Glu Trp Ser Pro Cys Ser Val Thr Cys Gly Asn Gly Ile Gln Val Arg
 1               5                  10                  15

Ile Lys Pro Gly Ser Ala Asn
 20

(2) INFORMATION FOR SEQ ID NO: 34:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO: 34:

Pro Val Ala Thr Asp Glu Trp Ser Pro Cys Ser Val Thr Cys Gly Asn
 1               5                  10                  15
```

Gly Ile Gln Val Arg Ile Lys Pro Gly Ser Ala Asn Pro Ala Thr Ser
20                  25                  30

Ser (2) INFORMATION FOR SEQ ID NO: 35:

(i) SEQUENCE CHARACTERISTICS:
        (A) LENGTH:  99 bases
        (B) TYPE:  nucleic acid
        (C) STRANDEDNESS:  single
        (D) TOPOLOGY:  linear (ii) MOLECULE TYPE:  nucleic acid (xi) SEQUENCE DESCRIPTION:  SEQ ID NO: 35:

CGAACTGGTG GCTGGATTAG CAGAGCCAGG CTTTATTCTA ACTTGTATAC                50

CATTTCCACA AGTTACACTA CATGGGGACC ATTCATCTGT TGCAACCGG                 99

(2) INFORMATION FOR SEQ ID NO: 36:

(i) SEQUENCE CHARACTERISTICS:
        (A) LENGTH:  33 nucleic acids
        (B) TYPE:  nucleic acid
        (C) STRANDEDNESS:  single
        (D) TOPOLOGY:  linear (ii) MOLECULE TYPE:  nucleic acid (xi) SEQUENCE DESCRIPTION:  SEQ ID NO: 36:

ACCATTTCCA CAAGTTACAC TACATGGGGA CCA                                  33

(2) INFORMATION FOR SEQ ID NO: 37:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  nucleic acid (xi) SEQUENCE DESCRIPTION:  SEQ ID NO: 37:

CCTCGTGCGA TTACGTCGGC                                                 20

(2) INFORMATION FOR SEQ ID NO: 38:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  nucleic acid (xi) SEQUENCE DESCRIPTION:  SEQ ID NO: 38:

AGCTGATAGA TTGATTGAGG                                                 20

(2) INFORMATION FOR SEQ ID NO: 39:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  nucleic acid (xi) SEQUENCE DESCRIPTION: SEQ ID NO: 39:

TCGACGTTGG GTAAATACCC                                                  20

(2) INFORMATION FOR SEQ ID NO: 40:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 40:

CCAAGGGACA CATTAGCAGG                                                  20

(2) INFORMATION FOR SEQ ID NO: 41:

(i) SEQUENCE CHARACTERISTICS:
        (A) LENGTH: 20 bases
        (B) TYPE: nucleic acid
        (C) STRANDEDNESS: single
        (D) TOPOLOGY: unknown (ii) MOLECULE TYPE: nucleic acid (xi) SEQUENCE DESCRIPTION: SEQ ID NO: 41:

TGGTATAACA TGGCGTTTGG                                                  20

(2) INFORMATION FOR SEQ ID NO: 42:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 42:

GCTGACAGTC CACTAATACC                                                  20

(2) INFORMATION FOR SEQ ID NO: 43:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 43:

GCTGCTGCAA GCAACATTCC                                                  20

(2) INFORMATION FOR SEQ ID NO: 44:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 44:

CACAGAATTC ATTAAAGAGG AG                                               22

-continued

```
(2) INFORMATION FOR SEQ ID NO: 45:

(i) SEQUENCE CHARACTERISTICS:
          (A) LENGTH:  17 amino acids
          (B) TYPE:  amino acid
          (C) STRANDEDNESS: Not Relevant
          (D) TOPOLOGY:  unknown (ii) MOLECULE TYPE:  peptide (iii) SEQUENCE DESCRIPTION:  SEQ ID NO: 45:

Cys Asp Lys Glu Leu Leu Pro Lys Val Asn Asn His Asp Cys Gln Ile
1               5                   10                  15

Ser (2) INFORMATION FOR SEQ ID NO: 46:

(i) SEQUENCE CHARACTERISTICS:
          (A) LENGTH:  16 amino acids
          (B) TYPE:  amino acid
          (C) STRANDEDNESS: Not Relevant
          (D) TOPOLOGY:  unknown (ii) MOLECULE TYPE:  peptide (iii) SEQUENCE DESCRIPTION:  SEQ ID NO: 46:

Asp Lys Glu Leu Leu Pro Lys Val Asn Asn His Asp Cys Gln Ile Ser
1               5                   10                  15
```

I claim:

1. A chimeric protein which comprises a Flock House virus capsid protein free from deletions, having a core structure constituted by anti-parallel beta barrels, and a heterologous peptide segment in a loop formed by said capsid protein in the region between beta-E and beta-F strands on one of said beta barrels.

2. An immunogenic composition comprising the chimeric protein of claim 1.

3. A diagnostic kit comprising the chimeric protein of claim 1.

4. A chimeric virus-like particle comprising a capsid including at least one chimeric protein of claim 1.

5. An immunogenic composition comprising the chimeric virus-like particle of claim 4.

6. A method of inducing an immune response in an animal comprising the step of administering an effective amount of a chimeric protein defined by claim 1 in a pharmaceutically accetptable excipient.

7. A chimeric protein which comprises a Flock House virus capsid protein free from deletions and including a heterologous peptide segment in the region between amino acid residues 205 and amino acid residue 209 from the amino terminus of said capsid protein, wherein said chimeric protein can assemble into a virus-like particle.

8. The chimeric protein of claim 4 wherein the heterologous protein segment has an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

9. The chimeric protein of claim 7 wherein the heterologous protein segment is represented by SEQ ID NO:1.

10. The chimeric protein of claim 7 wherein the heterologous protein segment is represented by SEQ ID NO:2.

11. The chimeric protein of claim 7 wherein the heterologous protein segment is represented by SEQ ID NO:3.

12. The chimeric protein of claim 7 wherein the heterologous protein segment is represented by SEQ ID NO:4.

13. The chimeric protein of claim 7 wherein the heterologous protein segment is represented by SEQ ID NO:5.

14. The chimeric protein of claim 7 wherein the heterologous protein segment is represented by SEQ ID NO:6.

15. The chimeric protein of claim 7 wherein the heterologous protein segment is represented by SEQ ID NO:7.

16. The chimeric protein of claim 7 wherein the heterologous protein segment is represented by SEQ ID NO:8.

17. The chimeric protein of claim 7 wherein the heterologous protein segment is represented by SEQ ID NO:9.

18. The chimeric protein of claim 7 wherein the heterologous peptide comprises at least one cell-specific targeting sequence chosen from the group consisting of a B cell epitope, a T cell epitope, a CTL epitope and a hepatocyte targeting sequence.

19. The chimeric protein of claim 7 wherein the heterologous peptide includes both a B cell epitope and a T cell epitope.

20. An immunogenic composition comprising the chimeric protein of claim 7.

21. A diagnostic kit comprising the chimeric protein of claim 7.

22. A chimeric virus-like particle comprising a capsid including at least one chimeric protein of claim 7.

23. An immunogenic composition comprising the chimeric virus-like particle of claim 22.

24. A method of inducing an immune response in an animal comprising the step of administering an effective amount of a chimeric protein defined by claim 7 in a pharmaceutically acceptable excipient.

* * * * *

UNITED STATES PATENT AND TRADEMARK OFFICE
CERTIFICATE OF CORRECTION

PATENT NO. : 6,171,591 B1
DATED : January 9, 2001
INVENTOR(S) : Stephen G. Hall

Page 1 of 1

It is certified that error appears in the above-identified patent and that said Letters Patent is hereby corrected as shown below:

Column 3, Table 1, 2nd column,
Under the heading "Insert Size",
2nd data entry, "7.5 kB" should be -- <7.5kB --.
3rd data entry, "4 kB" should be -- <4 kB --.
4th data entry, "20 kB" should be -- <20 kB --.
5th data entry, "25 kB" should be -- <25 kB --.
6th data entry, "20 kB" should be -- >20 kB --.

Column 4, Table 1 2nd column,
Under the heading "Insert Size"
1st data entry, "20 kB" should be -- >20 kB --.
2nd data entry, "20 kB" should be -- >20 kB --.

Column 10,
Line 7, "N $\leq$180" should be -- N$\leq$180 --.
Line 9, "N $\leq$30" should be -- N$\leq$30 --.

Columns 13-14, Table 3, 1st column,
Under the heading "Viral Epitope",
Line 23, "Gln" (first occurrence) should be -- Glu --.

Column 16,
Line 1, "$(r_k^-, m_k^{30})$" should be -- $(r_k^-, m_k^+)$ --.

Signed and Sealed this

Twenty-fifth Day of December, 2001

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,171,591 B1 Page 1 of 1
APPLICATION NO. : 08/986659
DATED : January 9, 2001
INVENTOR(S) : Stephen G. Hall It is certified that error appears in the above-identified patent and that said Letters Patent is hereby corrected as shown below:

Column 45,
Line 57, "claim 4" should be -- claim 7 --.
Line 58, "protein segment" should be -- peptide segment --.
Line 63, "protein segment" should be -- peptide segment --.
Line 65, "protein segment" should be -- peptide segment --.
Line 67, "protein segment" should be -- peptide segment --.

Column 46,
Line 34, "protein segment" should be -- peptide segment --.
Line 36, "protein segment" should be -- peptide segment --.
Line 38, "protein segment" should be -- peptide segment --.
Line 40, "protein segment" should be -- peptide segment --.
Line 42, "protein segment" should be -- peptide segment --.
Line 44, "protein segment" should be -- peptide segment --.

Signed and Sealed this

Twenty-first Day of October, 2008

JON W. DUDAS
*Director of the United States Patent and Trademark Office*